United States Patent
Wang et al.

(10) Patent No.: US 9,260,469 B2
(45) Date of Patent: Feb. 16, 2016

(54) METHOD OF PREPARATION OF ANTIVIRAL COMPOUNDS AND USEFUL INTERMEDIATES THEREOF

(75) Inventors: Yanling Wang, Shanghai (CN); Yuan Wang, Shanghai (CN); Xungui He, Shanghai (CN); Chuanjun Liu, Shanghai (CN); Jirang Zhu, Shanghai (CN); Jie Li, Shanghai (CN); Qingzhong Cheng, Shanghai (CN); Mingyong Yuan, Shanghai (CN)

(73) Assignee: ContraVir Pharmaceuticals, Inc., Edison, NJ (US)

(*) Notice: Subject to any disclaimer, the term of this patent is extended or adjusted under 35 U.S.C. 154(b) by 243 days.

(21) Appl. No.: 13/878,303

(22) PCT Filed: Oct. 7, 2011

(86) PCT No.: PCT/US2011/055229
§ 371 (c)(1),
(2), (4) Date: Aug. 20, 2013

(87) PCT Pub. No.: WO2012/048202
PCT Pub. Date: Apr. 12, 2012

(65) Prior Publication Data
US 2013/0331561 A1    Dec. 12, 2013

(30) Foreign Application Priority Data

Oct. 9, 2010 (CN) .......................... 2010 1 0506554
Nov. 16, 2010 (CN) .......................... 2010 1 0556506

(51) Int. Cl.
| | | |
|---|---|---|
| *C07H 19/20* | (2006.01) | |
| *C07H 19/04* | (2006.01) | |
| *A01N 43/04* | (2006.01) | |
| *A61K 31/70* | (2006.01) | |
| *C07H 19/24* | (2006.01) | |
| *A61K 31/519* | (2006.01) | |
| *C07H 19/073* | (2006.01) | |

(52) U.S. Cl.
CPC .............. *C07H 19/24* (2013.01); *A61K 31/519* (2013.01); *C07H 19/073* (2013.01)

(58) Field of Classification Search
CPC ..... A61K 31/519; C07H 19/24; C07H 19/073
See application file for complete search history.

(56) References Cited

U.S. PATENT DOCUMENTS

| | | | |
|---|---|---|---|
| 5,302,707 A | 4/1994 | Campbell et al. | |
| 8,329,664 B2 * | 12/2012 | McGuigan et al. | 514/43 |
| 8,513,215 B2 * | 8/2013 | Balzarini et al. | 514/49 |
| 8,912,163 B2 * | 12/2014 | Balzarini et al. | 514/49 |
| 2010/0256087 A1 | 10/2010 | Balzarini et al. | |

FOREIGN PATENT DOCUMENTS

| | | |
|---|---|---|
| WO | WO-0183501 A1 | 11/2001 |
| WO | WO-2007129083 A1 | 11/2007 |
| WO | WO 2009/030410 A1 * | 3/2009 |

OTHER PUBLICATIONS

De Clercq. "Antiviral Drug Discovery: Ten More Compounds, and Ten More Stories (Part B)." *Med. Res. Rev.* 29.4(2009):571-610.
McGuigan et al. "Preclinical Development of Bicyclic Nucleoside and Analogues as Potent and Selective Inhibitors of Varicella Zoster Virus." *J. Antimicrob. Chemo.* 60(2007):1316-1330.

* cited by examiner

*Primary Examiner* — Lawrence E Crane
(74) *Attorney, Agent, or Firm* — Cooley LLP; Ivor R. Elrifi; Heidi A. Erlacher

(57) ABSTRACT

The invention is directed to processes for synthesizing bicyclic nucleoside antiviral compounds and for synthesizing the intermediates used in the process. The invention is also directed to novel intermediate compounds useful in the process. The antiviral compounds are useful in the treatment of herpes zoster (i.e., varicella zoster virus, VZV, shingles) and for the prevention of post herpetic neuralgia (PHN) resulting from this viral infection.

15 Claims, 3 Drawing Sheets

XRDP of Polymorph I and Polymorph II mixture

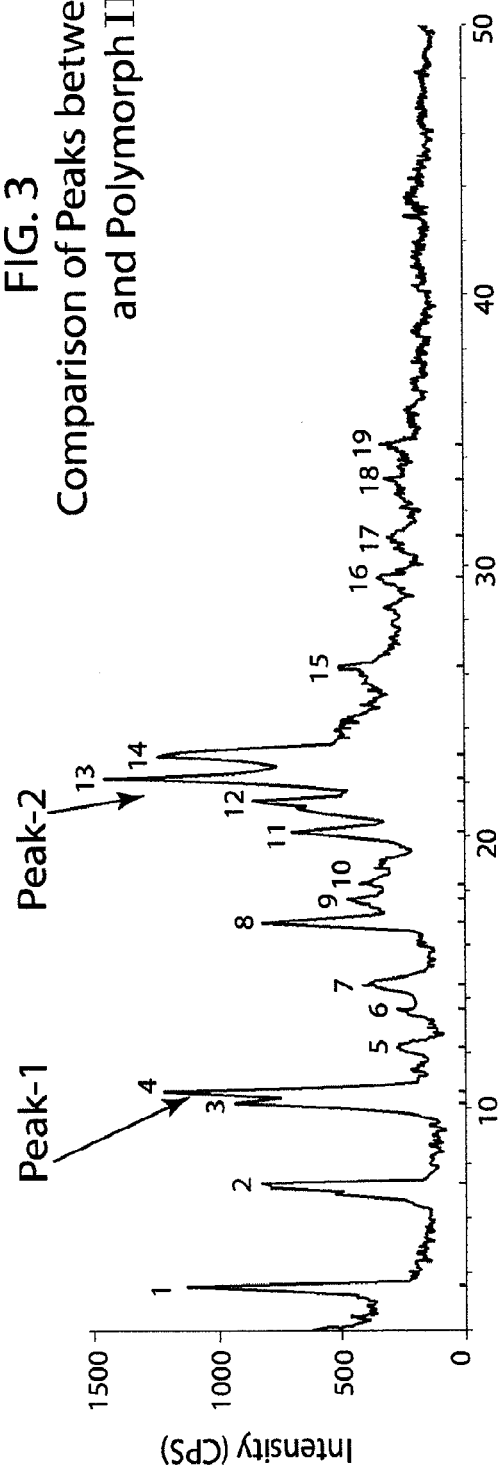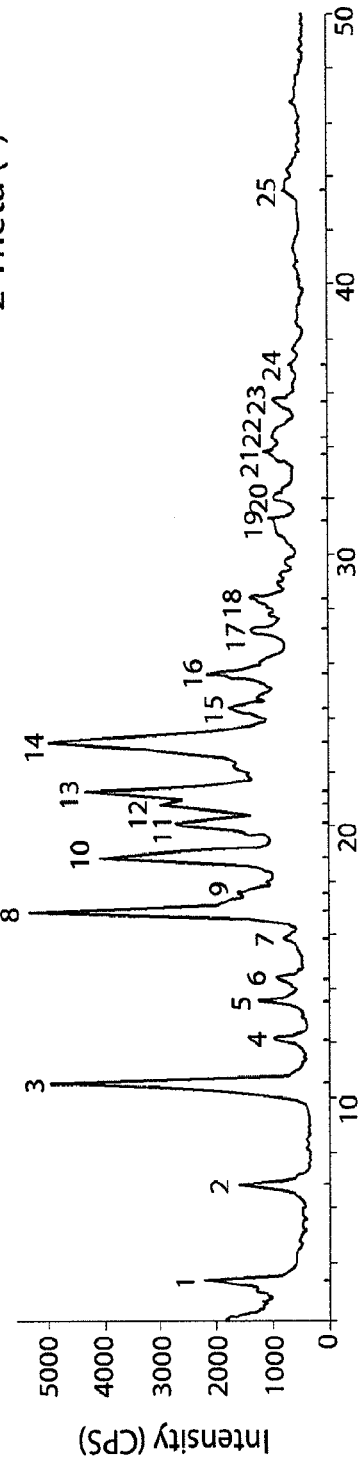
FIG. 3
Comparison of Peaks between mixture and Polymorph II
Picture-1: XRPD of the Mixture of the two Polymorphic Forms [(I) and (II)]
Picture-2: XRPD of the pure Polymorphic Form II

METHOD OF PREPARATION OF ANTIVIRAL COMPOUNDS AND USEFUL INTERMEDIATES THEREOF

CROSS REFERENCE TO RELATED APPLICATIONS

The present application claims priority to Chinese Patent Application Ser. No. 201010506554.0, filed Oct. 9, 2010, and Chinese Patent Application Ser. No. 201010556506.2, filed Nov. 16, 2010, the entire disclosures of which are incorporated herein by reference.

FIELD OF THE INVENTION

This application relates to methods for the preparation of a synthetic active pharmaceutical ingredient, FV-100, (S)-((2R,3S,5R)-(3-hydroxy-5-(2-oxo-6-(4-pentylphenyl)furo[2,3-d]pyrimidin-3(2H)-yl)-tetrahydrofuran-2-yl)methyl 2-amino-3-methylbutanoate hydrochloride, a bicyclic nucleoside compound, useful in the treatment of herpes zoster (i.e., varicella zoster virus, VZV, shingles) and for the prevention of post-herpetic neuralgia (PHN) resulting from this viral infection. The invention also relates to the methods for purification of FV-100 and the methods for transformation of polymorphic forms of FV-100. In addition the invention relates to novel compounds useful as intermediates in the preparation of the active drug material.

BACKGROUND OF THE INVENTION

Herpes zoster, also known as shingles, results from the reactivation of the virus that causes chickenpox (varicella zoster virus). The virus may spread from one or more ganglia along nerves of an affected segment and infect the corresponding dermatome (an area of skin supplied by one spinal nerve) causing a painful rash. Although the rash usually heals within two to four weeks, some sufferers experience residual nerve pain for months or years, a condition called postherpetic neuralgia.

Throughout the world the incidence rate of herpes zoster every year ranges from 1.2 to 3.4 cases per 1,000 healthy individuals, increasing to 3.9-11.8 per year per 1,000 individuals among those older than 65 years. In early-clinical studies, the bicyclic nucleoside analogue FV-100 has proven to be the most potent antiviral available against this family of viruses.

WO 2001/083501A1, the contents of which are incorporated herein by reference, describes certain nucleoside analogues with potent activity against Varicella Zoster virus (VZV), said nucleoside analogues having general Formula (I):

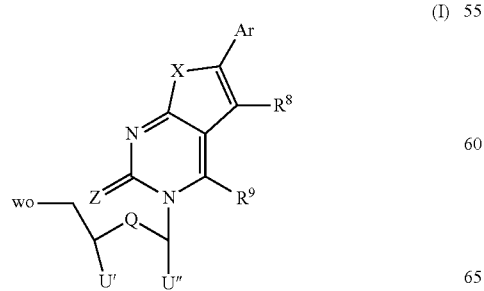

(I)

wherein:
Ar is an optionally substituted, aromatic ring system, the aromatic ring system comprising one six-membered aromatic ring or two fused six-membered aromatic rings;
$R^8$ and $R^9$ are each independently selected form the group comprising hydrogen, alkyl, cycloalkyl, halogens, amino, alkylamino, dialkylamino, nitro, cyano, alkyloxy, aryloxy, thiol, alkylthiol, arylthiol, aryl;
Q is selected from the group comprising O, S, and $CY_2$, where Y may be the same or different and is selected from H, alkyl and halogens;
X is selected from the group comprising O, NH, S, N-alkyl, $(CH_2)_m$, where m is 1 to 10, and $CY_2$ where Y may be the same or different and is selected from hydrogen, alkyl and halogens;
Z is selected from the group comprising O, S, NH, and N-alkyl;
U" is H and U' is selected from H and $CH_2T$, or
U' and U" are joined so as to form a ring moiety including Q wherein U'-U" together is respectively selected from the group comprising CT"H-CT'T" and CT'=CT', so as to provide ring moieties selected from the group comprising

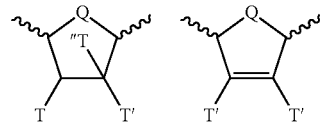

wherein T is selected from the group comprising OH, H, halogens, O-alkyl, O-acyl, O-aryl, CN, $NH_2$ and $N_3$;
T' is selected from the group comprising H and halogens and, where more than one T' is present, they may be the same or different;
T" is selected from the group comprising H and halogens; and
W is selected from the group comprising H, a phosphate group, and a phosphonate group
and a pharmacologically acceptable salt, derivative, or prodrug thereof;
with the proviso that when T is OAc, and T' and T" are present and are H, Ar is not 4-(2-benzoxazolyl)phenyl.

Compounds 1 and 2 below are particularly preferred compounds according to WO 2001/083501A1:

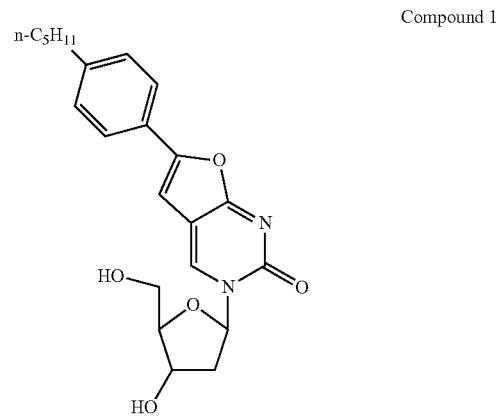

Compound 1

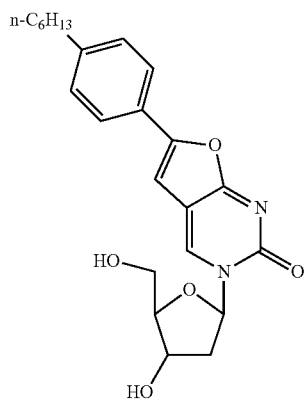

Compound 2

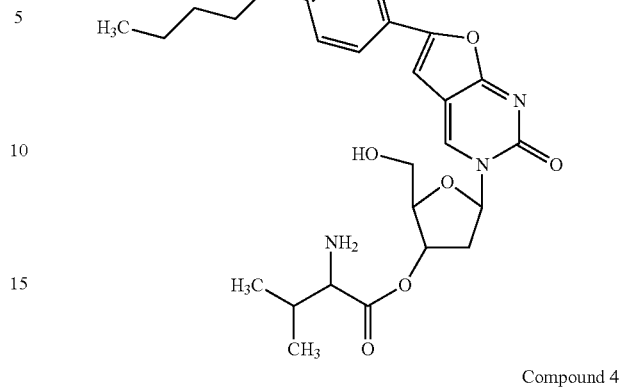

Compound 3

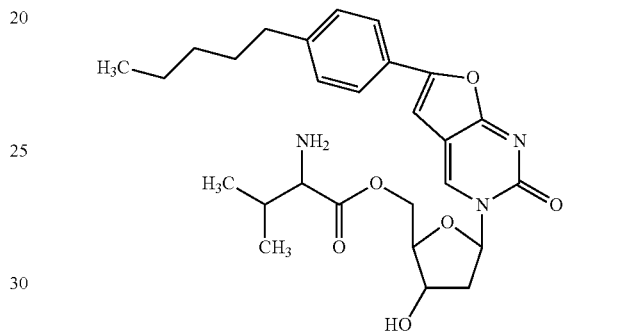

Compound 4

WO 2007/129083 A1, the contents of which are incorporated herein by reference, discloses derivatives of Formula (II):

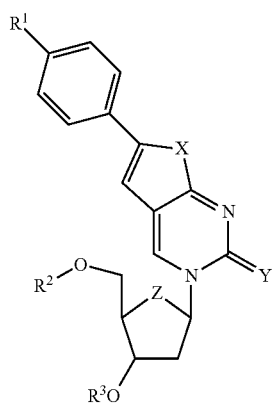

(II)

wherein X is O, S, NH or CH₂;
Y is O, S or NH;
Z is O, S or CH₂;
R¹ is $C_{1-6}$ alkyl, preferably n-alkyl, e.g., n-pentyl or n-hexyl;
one of R² and R³ is H, and the other of R³ and R² is a neutral, non-polar amino acid moiety;
or a pharmaceutically acceptable salt or hydrate thereof.

Compounds 3 and 4 below are particularly preferred compounds according to WO 2007/129083 A1:

WO 2007/129083 A1 also discloses a method of synthesizing a compound of Formula (II) comprising esterifying a compound of Formula (III):

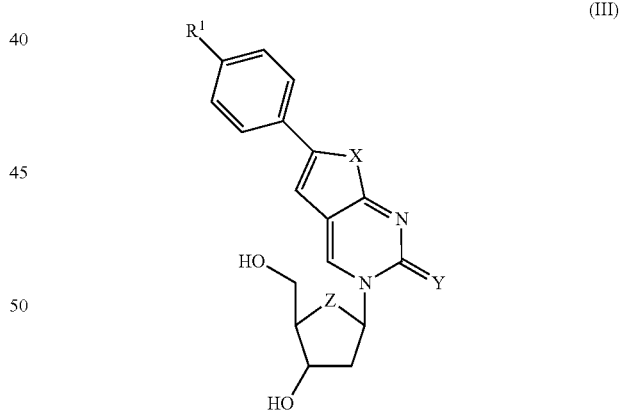

(III)

with a protected neutral, non-polar amino acid, wherein R¹, X, Y and Z are as defined above for Formula (II).

In the disclosed example for the preparation of Compound 3, the hydroxymethyl nucleoside precursor, Compound 1 is converted to the L-valine final product under conditions employing resin-bound triphenylphosphine and Fmoc-protected valine. Using resin bound reagent facilitates removal of the side product, triphenyl phosphine oxide by filtration, however, the high cost and large volumes required for resin-bound triphenylphosphine makes this method of preparation impractical for scale up purposes. Moreover, due to the poor selectivity between the primary and secondary hydroxyl groups, the bis-valine substituted byproduct can be significant, in which case isolation of sufficiently pure compound FV-100 would require purification by column chromatography.

Methods of preparation that allow production of compounds of Formula (II) in practical yields, are adaptable to large scale preparation, and avoid costly reagents are therefore of value and useful.

SUMMARY OF THE INVENTION

The present invention describes a novel process for the synthesis of a nucleoside amino acid ester of Formula (IV) [Formula (II) where X, Y and Z are O, $R^2$ is $(R^4R^5CHCH(NH_2)C(=O)$—, and $R^3$ is H] from a compound of Formula (IIIa):

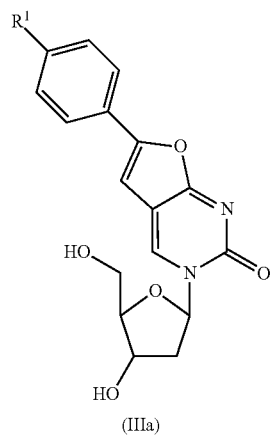

(IIIa)

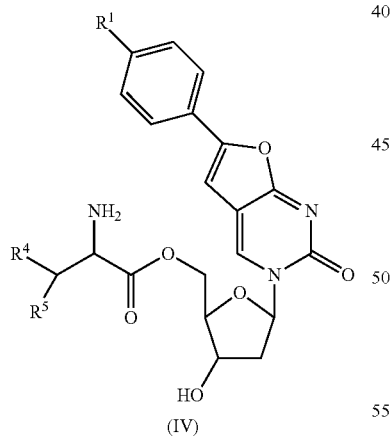

(IV)

wherein $R^1$ is $C_1$-$C_6$ alkyl;

$R^4$ and $R^5$ are each independently H or $C_1$-$C_2$ alkyl; and the pharmaceutically acceptable salts and hydrates thereof.

The present invention also describes novel processes for the synthesis of compounds of Formulae (V)-(VIII):

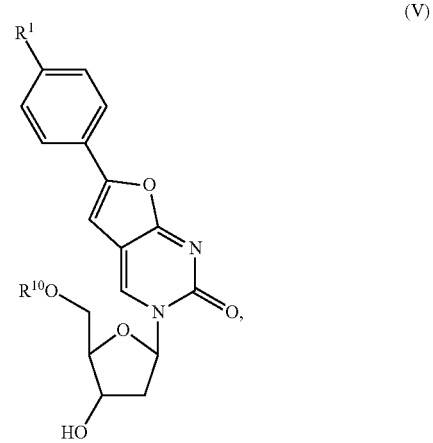

(V)

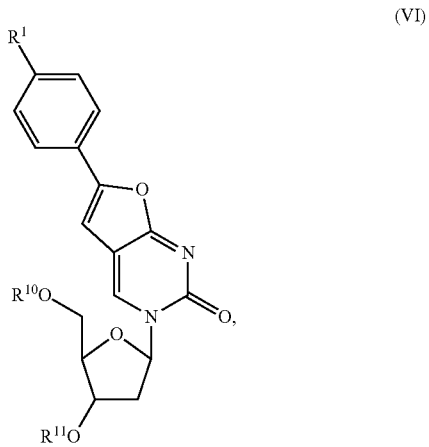

(VI)

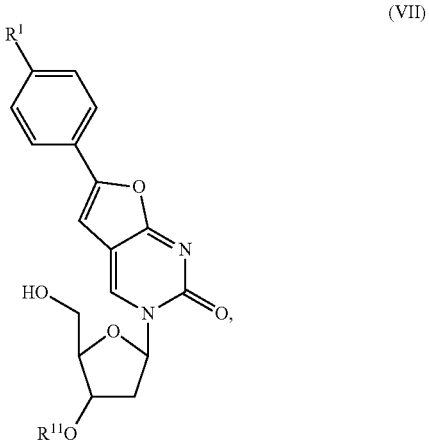

(VII)

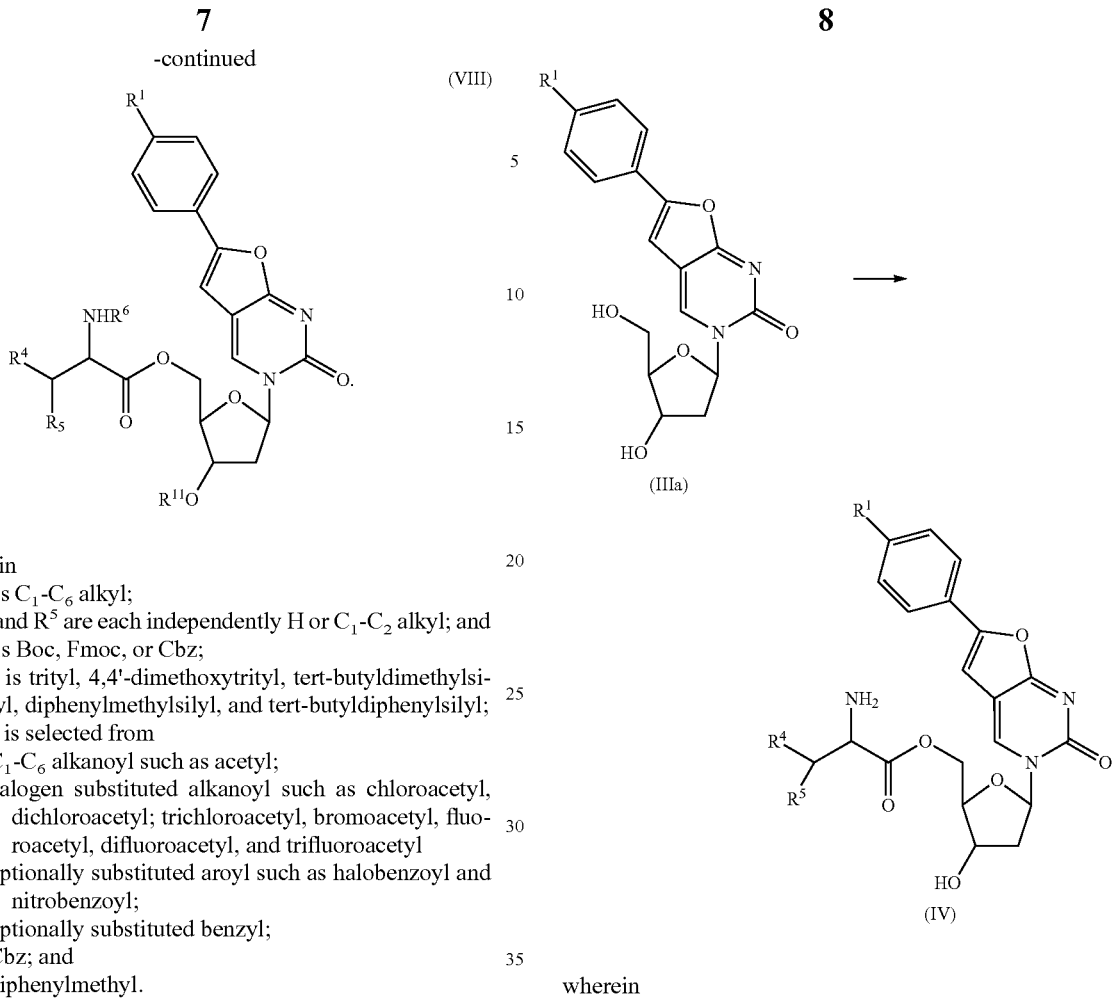

(VIII)

wherein
$R^1$ is $C_1$-$C_6$ alkyl;
$R^4$ and $R^5$ are each independently H or $C_1$-$C_2$ alkyl; and
$R^6$ is Boc, Fmoc, or Cbz;
$R^{10}$ is trityl, 4,4'-dimethoxytrityl, tert-butyldimethylsilyl, diphenylmethylsilyl, and tert-butyldiphenylsilyl;
$R^{11}$ is selected from
  $C_1$-$C_6$ alkanoyl such as acetyl;
  halogen substituted alkanoyl such as chloroacetyl, dichloroacetyl; trichloroacetyl, bromoacetyl, fluoroacetyl, difluoroacetyl, and trifluoroacetyl
  optionally substituted aroyl such as halobenzoyl and nitrobenzoyl;
  optionally substituted benzyl;
  Cbz; and
  diphenylmethyl.

The compound of Formula (IV) is useful in the treatment of patients infected with varicella zoster (shingles). The compounds of Formulae (V)-(VIII) are intermediates, useful for the preparation of the Formula (IV) compound.

The present invention also describes a process for the purification of the hydrochloride salt of the compound of Formula (IV), where $R^1$ is n-pentyl and $R^4$ and $R^5$ are methyl, i.e., Compound 4HCl salt, FV-100.

In addition, the present invention also describes polymorphic forms (I and II) of the hydrochloride salt of Compound 4, and a process for the transformation of polymorphic form (I) or a mixture of polymorphic forms (I and II) of the hydrochloride salt of Compound 4 into its polymorphic form (II)

BRIEF DESCRIPTION OF THE DRAWING FIGURES

FIG. 3 shows a comparison of peaks between the Mixture and Polymorph Form II

DETAILED DESCRIPTION OF THE INVENTION

Figure 1:
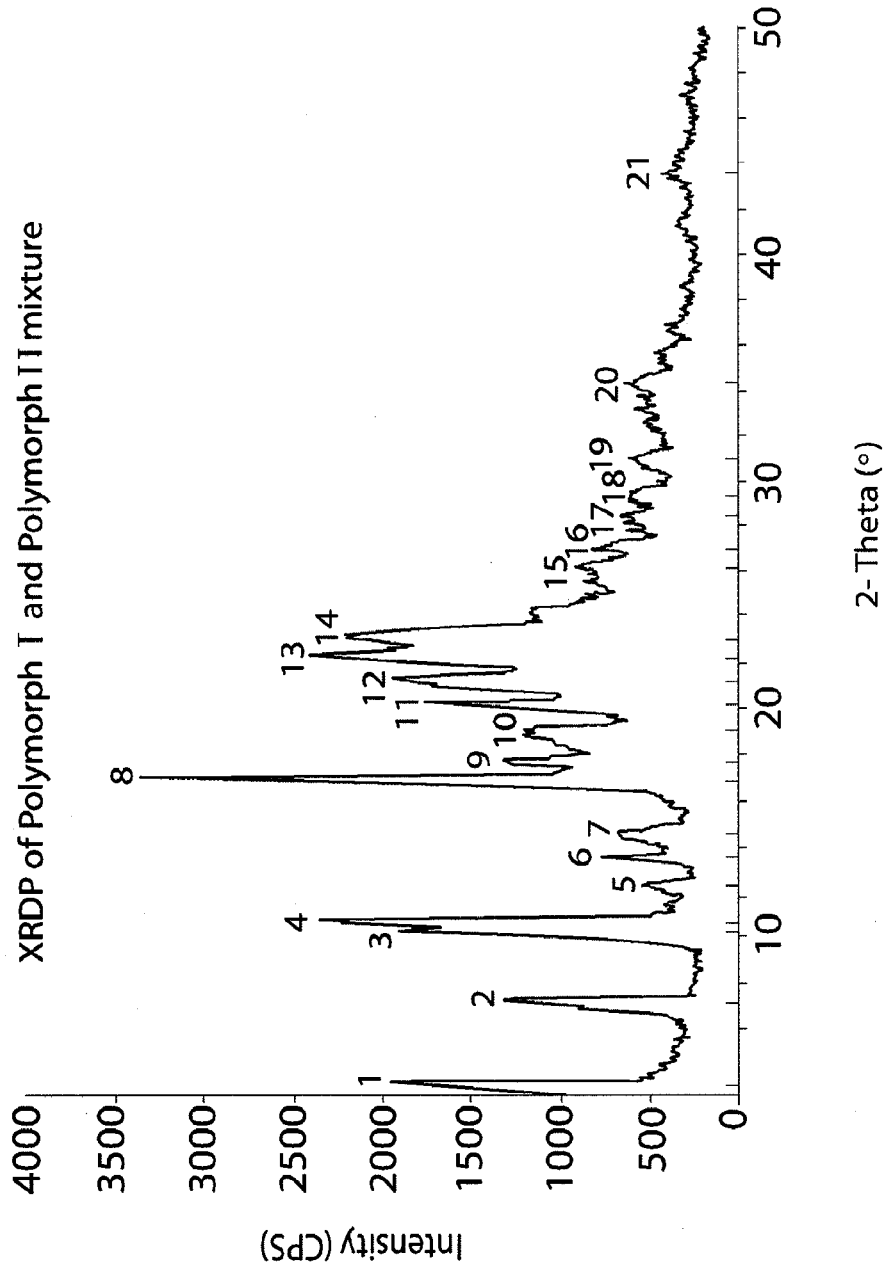
FIG. 1 is the X-Ray Powder Diffraction (XRPD) pattern for a mixture of the two Polymorphic Forms [(I) and (II)] of the hydrochloride salt of Compound 4.

The invention is directed to process to synthesize 2-deoxy-nucleoside amino acid esters of Formula (IV) from the compound of Formula (IIIa):

(IIIa)

(IV)

wherein
$R^1$ is $C_1$-$C_6$ alkyl;
$R^4$ and $R^5$ are each independently H or $C_{1-2}$ alkyl; and
the pharmaceutically acceptable salts and hydrates thereof;

comprising the steps of
(1) protection of the primary hydroxyl group in the compound of Formula (IIIa) to form a first intermediate compound of Formula (V);
(2) protection of the secondary hydroxyl group in the intermediate compound of Formula (V) to form a second intermediate compound of Formula (VI);
(3) deprotection of primary hydroxyl group in the said second intermediate of Formula (VI) to form a third intermediate of Formula (VII);
(4) esterification of primary hydroxyl group in the said third intermediate of Formula (VII) with a protected amino acid to form a fourth intermediate of Formula (VIII);
(5) deprotection of secondary hydroxyl group and amino acid group in the said fourth intermediate of Formula (VIII) to form the compound Formula (IV), and
(6) optionally conversion the said compound of Formula (IV) to a pharmaceutically acceptable salt or hydrate thereof.

The process is illustrated in the flow diagram of Scheme 1 below. As shown in Scheme 1, the process includes the multiple steps in converting the starting material, nucleoside of Formula (IIIa), to the finished product of Formula (IV).

SCHEME 1
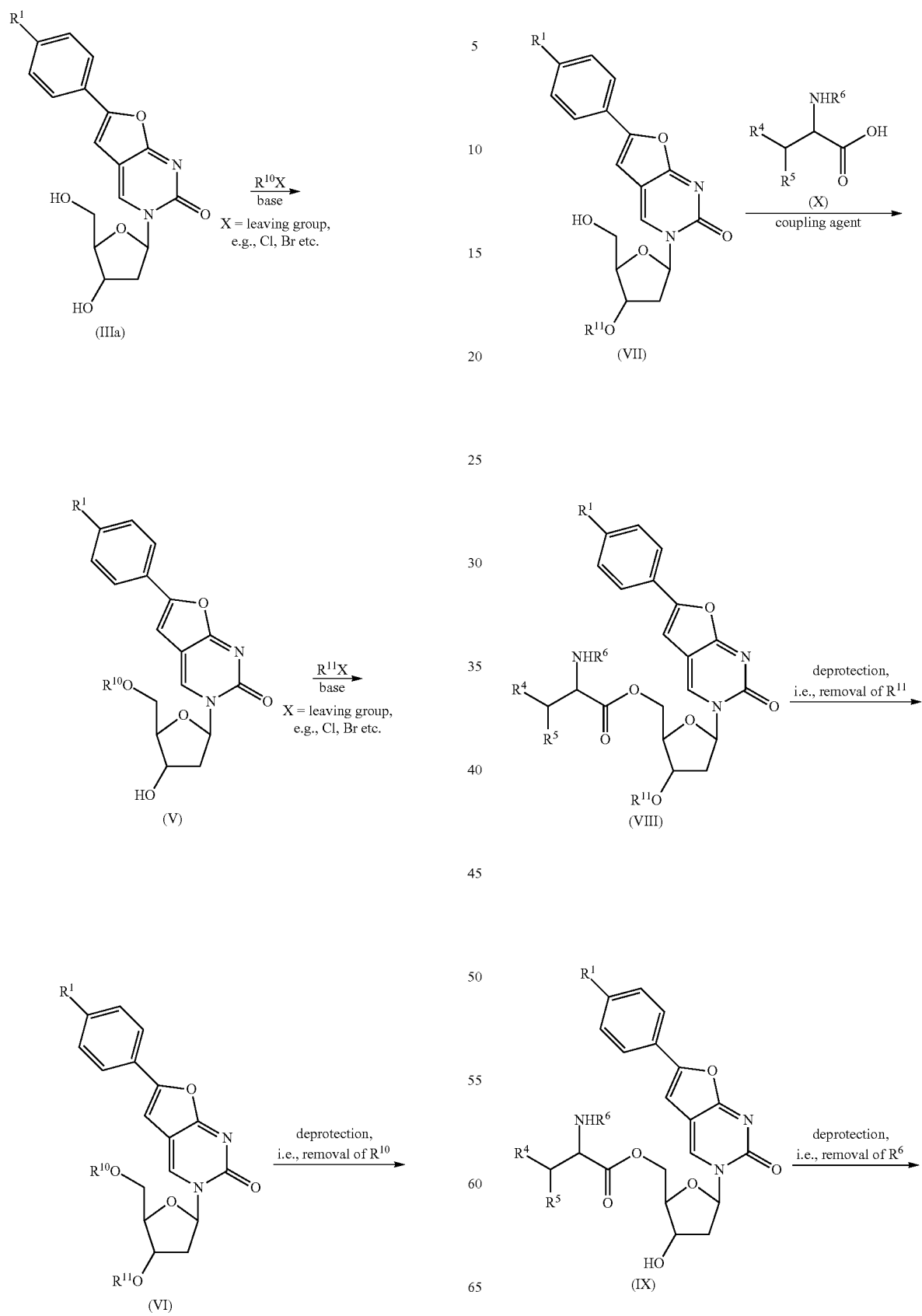

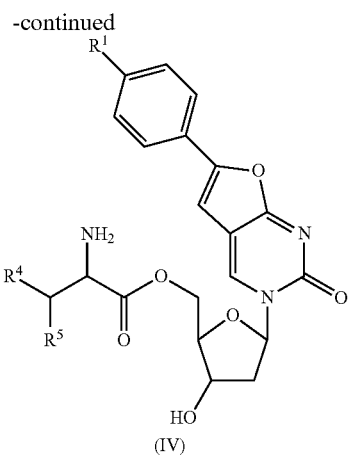

(IV)

Scheme 1 illustrates the process of this invention as employed to synthesize compounds of Formula (IV) As shown, the starting material is the nucleoside of Formula (IIIa), prepared as described in the WO 2001/083/501 A1 (see Example 3, page 15).

Step one of the process is the reaction of the Formula (IIIa) compound with a reagent of Formula $R^{10}X$, i.e., protection of the primary hydroxyl group with a first protecting group $R^{10}$, in the presence of a base, to produce the intermediate of Formula (V), wherein $R^{10}$ represents a suitable protecting group of the primary hydroxyl moiety, X is a leaving group such as a halo or tosyl, an optionally substituted arylsulfonyl or an $C_1$-$C_6$ alkylsulfonyl group, and $R^1$ is as defined above. The term "leaving group" is contemplated in general to include any group capable of forming a leaving group, and any molecular group in which X will leave with a pair of electrons following a heterolytic bond cleavage, and will include both anions and neutral molecules. In addition to halo and the corresponding anionic (halide) groups such as $Cl^-$, $Br^-$, $I^-$, etc.; and sulfonate groups such as methanesulfonate or "mesylate", para-toluenesulfonate or "tosylate" ($TsO^-$), benzenesulfonate, para-bromobenzenesulfonate or "brosylate" ($BsO^-$), or 4-nitrobenzenesulfonate or "nosylate" ($NsO^-$)groups; other suitable leaving groups may include water ($H_2O$), ammonia ($NH_3$), and alcohols (ROH).

Suitable $R^{10}$ protecting groups are those which can be introduced selectively to the primary hydroxyl group with minimal or no concurrent reaction with secondary hydroxyl group present in the Formula (IIIa) compound, and which can be cleaved under non-basic condition or catalytic hydrogenation, For example, suitable $R^{10}$ groups include trityl, 4,4'-dimethoxytrityl, bulky silyl groups such as tert-butyldimethylsilyl, diphenylmethylsilyl and tert-butyldiphenylsilyl and others well known in the art of organic synthesis.

Suitable bases include pyridine, tertiary amines such as triethylamine, DMAP, imidazole and the like.

The reaction may optionally be carried out in a suitable inert solvent or the base itself, e.g., pyridine, which can serve as the solvent. Suitable inert solvents include dichloromethane and the like.

The process is carried out at a temperature sufficient to promote reaction, generally from about 0° C. to about 50° C., preferably at ambient temperature (room temperature).

Step two of the process is the reaction of the Formula (V) intermediate with a reagent of Formula $R^{11}X$, i.e., protection of the secondary hydroxyl group by a group $R^{11}$, in the optional presence of a suitable base, to produce the intermediate of Formula (VI), wherein $R^{11}$ represents a suitable protecting group of the secondary hydroxyl moiety, X is a leaving group such as halo or tosyl, and $R^1$ is as defined above, to produce the intermediate of Formula (VI).

Suitable protecting groups are those that can easily be cleaved under neutral to mildly basic conditions, mercaptans, or by catalytic hydrogenation. $R^{11}$ groups suitable for the secondary hydroxyl protection that are cleaved under neutral to mildly basic conditions include alkyl esters such as acetyl; halogen substituted alkyl esters such as chloroacetyl, dichloroacetyl, trichloroacetyl, bromoacetyl, fluoroacetyl, difluoroacetyl; trifluoroacetyl; substituted or non substituted aromatic esters such as halogen or nitro-substituted benzoyl. $R^{11}$ groups suitable for the secondary hydroxyl protection that are cleaved by catalytic hydrogenation (hydrogenolysis) include benzyl, Cbz, diphenylmethyl and the like, well known in the art of organic synthesis.

Suitable bases include pyridine, tertiary amines such as triethylamine, DMAP and the like.

The reaction may optionally be carried out in a suitable inert solvent or the base itself, e.g., pyridine, which can serve as the solvent. Suitable inert solvents include dichloromethane and the like.

The process is carried out at a temperature sufficient to promote reaction, generally from about 0° C. to about 50° C., preferably at ambient temperature (room temperature).

The intermediate compound of Formula (VI) may be isolated, or may be used directly in following steps without isolation or purification.

Step three of the process is the reaction (selective deprotection) of the intermediate of Formula (VI) under either acidic conditions or in the presence of a fluoride-containing reagent to produce to the intermediate of Formula (VII) where $R^1$ and $R^{11}$ are as defined above.

Depending on the nature of the protecting group, deprotection can be accomplished under various conditions. When the $R^{10}$ group is trityl or 4,4'-dimethoxytrityl and the like, deprotection can be carried out under acid conditions. Suitable acids useful to produce the acidic conditions are, for example, an organic acid such as acetic acid, trichloroacetic acid or trifluoroacetic acid (TFA), or a mineral acid such as hydrochloric acid and the like. When the $R^{10}$ group is a bulky silyl group such as tert-butyldimethylsilyl, diphenylmethylsilyl, or tert-butyldiphenylsilyl and the like, deprotection can be carried out with a fluoride-containing reagent such as sodium fluoride, potassium fluoride, or tetra-butylammonium fluoride.

The process can be carried out in a suitable solvent such as dichloromethane or water, DMF, THF. and the like or the organic acid itself can act as the solvent.

The process is carried out at a temperature sufficient to promote reaction, generally from about 0° C. to about 60° C., preferably from about 30 to about 35° C.

The intermediate compound of Formula (VII) may be isolated, or may be used directly in following steps without isolation or purification.

Step four of the process is the esterification of primary hydroxyl group in intermediate of Formula (VII) with a protected amino acid of Formula (X), optionally in the presence of a coupling (dehydrating) agent and a base, to form the intermediate compound of Formula (VIII), where $R^4$ and $R^5$ are independently H or $C_{1-2}$ alkyl; $R^6$ represents an amino acid protecting group selected from Boc, Fmoc, or Cbz; and $R^1$ and $R^{11}$ are as described above.

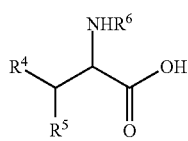

(X)

Suitable coupling (dehydrating) agents include dicyclohexylcarbodiimide (DCC) EDC, CDI, HOBT, PPh₃/Diethyl azodicarboxylate (DEAD), PPh₃/Diisopropyl azodicarboxylate (DIAD) and the like. Suitable bases include DMAP and the like. Suitable solvents are non-protic polar solvents such as THF and the like.

The process is carried out at a temperature sufficient to promote reaction, generally from about 0° C. to about 50° C., preferably at ambient (room) temperature.

Step five of the process is the deprotection of secondary hydroxyl protecting group $R^{11}$ and amino acid protecting group ($R^6$) in the intermediate of Formula (VIII), to provide the compound Formula (IV). Deprotection of the $R^{11}$ and $R^6$ groups can be accomplished using a suitable mild base and/or thio reagents, or combinations of bases and thio reagents thereof. Suitable mild bases useful in this step are bases such as pyrrole, piperidine, morpholine, 1,8-diazabicyclo[5.4.0]undec-7-ene (DBU) and sodium carbonate; suitable thio reagents are thiourea and mercaptans such as ethyl mercaptan, Alternatively, deprotection of the $R^{11}$ protecting group may be accomplished by mild bases or by catalytic hydrogenation (hydrogenolysis) for the deprotection of optionally substituted benzyl protecting groups.

The deprotection of the $R^{11}$ can be conducted first, and the intermediate of Formula (IX) may optionally be isolated. Alternatively, the deprotection of both the $R^{11}$ and $R^6$ groups can be conducted without isolation of intermediates, to provide the compound of Formula (IV) directly.

The basic deprotection reaction is carried out in a suitable inert solvent or the base itself, e.g., pyridine, which can serve as the solvent. Suitable inert solvents include dichloromethane and the like.

Suitable catalysts for catalytic hydrogenation include platinum, nickel, rhodium or palladium catalysts such as Raney Ni, Pd on C, Pt on C, Rh—C, Rh/Al₂O₃, and Pt₂O.

The hydrogenolysis deprotection reaction may be carried out in a suitable solvent such as protic solvents such as methanol, ethanol, formic acid and acetic acid, or inert solvents such as DMF(N,N-dimethylformamide), NMP(N-methylpyrrolidine), DMAC(N,N-dimethylacetamide), DMSO THF, 2-Me-THF, ethyl acetate, etc, or combination of the above.

The optional conversion of the compound of Formula (IV) to a pharmaceutically acceptable salt is accomplished by introducing an acid under anhydrous conditions, e.g., gaseous HCl into a solution of the compound of Formula (IV), or by addition of a solution of HCl in an organic solvent such as isopropanol (IPA), ethanol, or ethyl acetate (EA).

Recrystallization of the product of Formula (IV) obtained by the above processes can be carried under a variety of conditions described in the experimental section, using suitable solvents such as methanol, dichloromethane, methyl tert-butyl ether (MTBE) or mixtures thereof, in order to obtain purified product.

The above process is not necessarily carried out step by step. For example, the conversion of compound of Formula (IIIa) to the compound of Formula (VII), and likewise, the conversion of the compound of Formula (VII) to the compound of Formula (IV), each can be optionally and independently combined into one-pot procedures, thus reducing the number of separation operations.

In another aspect of the invention, there is provided a process for the synthesis of a compound of Formula (V) from the compound of Formula (IIIa):

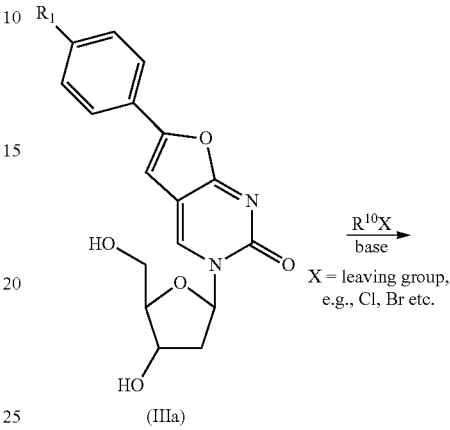

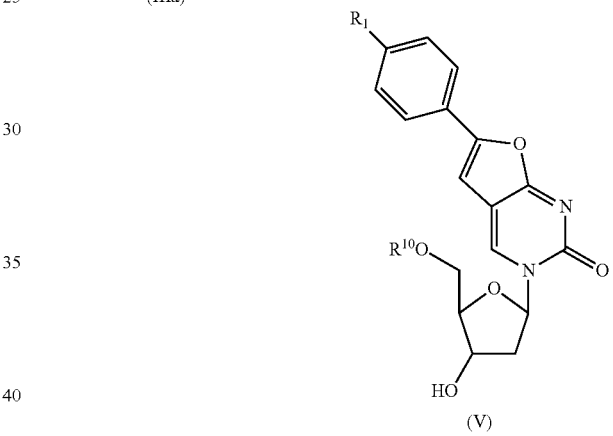

comprising the reaction of the primary hydroxyl group in said Formula (IIIa) compound with a reagent $R^{10}X$ in the optional presence of a suitable base, wherein $R^{10}$ is trityl, 4,4'-dimethoxytrityl, tert-butyldimethylsilyl, diphenylmethylsilyl or tert-butyldiphenylsilyl;

X is a leaving group such as halo, tosyl and the like; and $R^1$ is as defined above.

Suitable bases include pyridine, tertiary amines such as triethylamine, DMAP, imidazole and the like.

The reaction may optionally be carried out in a suitable inert solvent or the base itself, e.g., pyridine, which can serve as the solvent. Suitable inert solvents include dichloromethane and the like.

The process is carried out at a temperature sufficient to promote reaction, generally from about 0° C. to about 50° C., preferably at ambient temperature (room temperature).

The intermediate compound of Formula (V) may be isolated, or may be used directly in following steps with out isolation or purification.

In another aspect of the invention, there is provided a process for the synthesis of the compound of Formula (VI) from the compound of Formula (V):

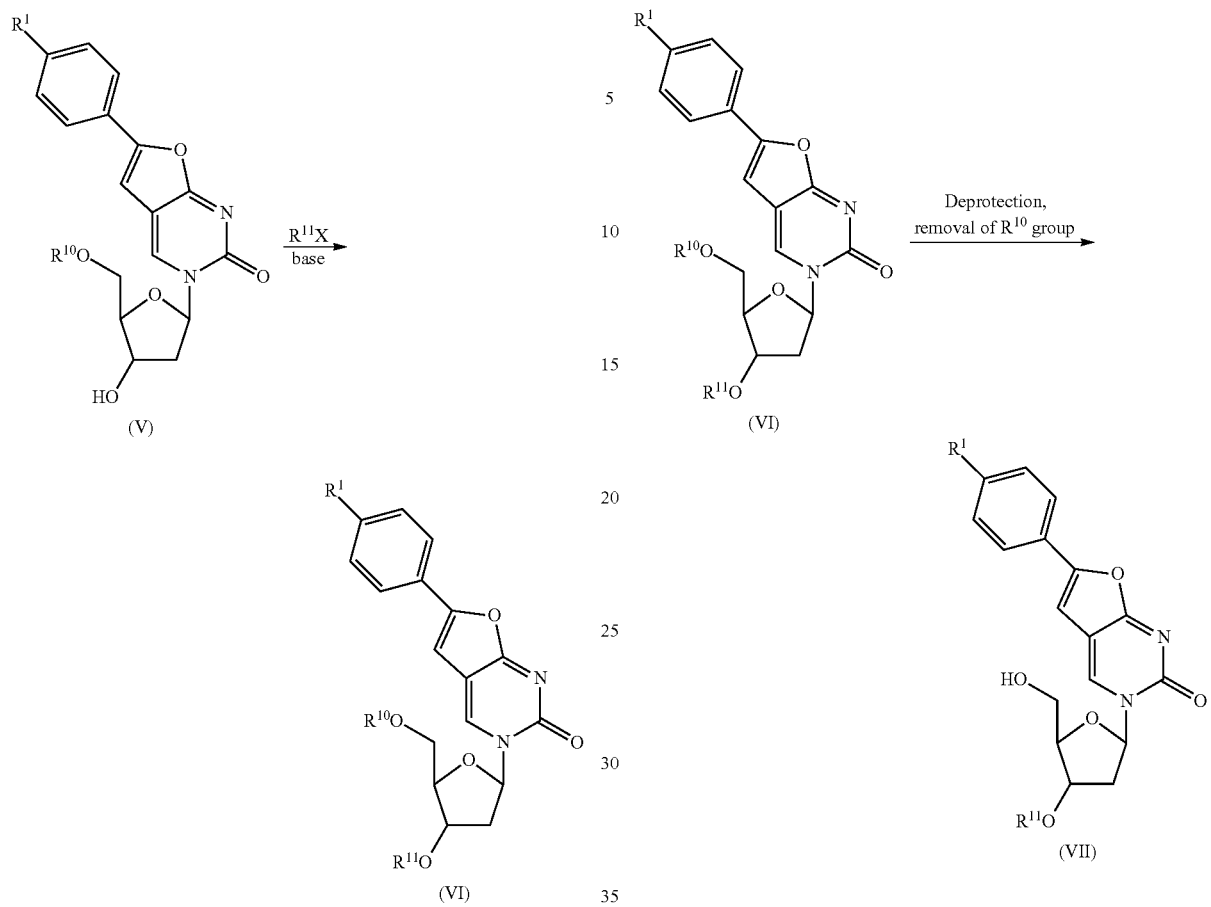

comprising reaction of the Formula (X) compound with a reagent $R^{11}X$ in the optional presence of a base, wherein $R^{11}$ is selected from $C_1$-$C_6$ alkanoyl such as acetyl;

halogen substituted alkanoyl such as chloroacetyl, dichloroacetyl, trichloroacetyl, bromoacetyl, fluoroacetyl, difluoroacetyl, and trifluoroacetyl;

optionally substituted aroyl such as halobenzoyl and nitrobenzoyl;

optionally substituted benzyl;

Cbz and diphenylmethyl;

X is a leaving group, such as halo, tosyl and the like; and $R^1$ and $R^{10}$ are as defined above.

Suitable bases include pyridine, tertiary amines such as triethylamine, DMAP, and the like.

The reaction may optionally be carried out in a suitable inert solvent such as dichloromethane and the like.

The process is carried out at a temperature sufficient to promote reaction, generally from about 0° C. to about 50° C., preferably at ambient temperature (room temperature)

In another aspect of the invention, there is provided a process for the synthesis of the compound of Formula (VII) from the compound of Formula (VI):

comprising reaction of the Formula (VI) compound under deprotection conditions wherein $R^1$, $R^{10}$, and $R^{11}$ are as defined above.

Deprotection of the $R^{10}$ group may be accomplished under acidic conditions, when $R^{10}$ is trityl or 4,4'-dimethoxytrityl. Acids useful to produce the acidic conditions are, for example, an organic acid such as acetic acid, trichloroacetic acid or trifluoroacetic acid (TFA), or a mineral acid such as hydrochloric acid and the like. When $R^{10}$ is a bulky silyl group, deprotection may be accomplished using a fluoride-containing reagent in a suitable solvent. Suitable fluoride-containing reagents include sodium fluoride, potassium fluoride and tetra-n-butylammonium fluoride.

The process can be carried out in a suitable solvent such as dichloromethane or water, DMF, THF. and the like or the organic acid itself can act as the solvent.

The process is carried out at a temperature sufficient to promote reaction, generally from about 0° C. to about 60° C., preferably from about 30 to about 35° C.

Deprotection of the $R^{10}$ group, when $R^{10}$ is a bulky silyl group, may be also accomplished under acidic conditions. Acids is useful to produce the acidic conditions are, for example, an organic acid such as trichloroacetic acid, trifluoroacetic acid (TFA), trifluorosulfonic acid or a mineral acid such as hydrochloric acid and the like. Or, the deprotection may be accomplished using a fluoride-containing reagent in a suitable solvent. Suitable fluoride-containing reagents include sodium fluoride, potassium fluoride and tetra-n-butylammonium fluoride. Suitable solvents include ethanol, DMF, THF. and the like.

The intermediate compound of Formula (VII) may be isolated, or may be used directly in following steps without isolation or purification.

In yet another aspect of the invention, there is provided a process for the synthesis of the compound of Formula (VIII) from the compound of Formula (VII):

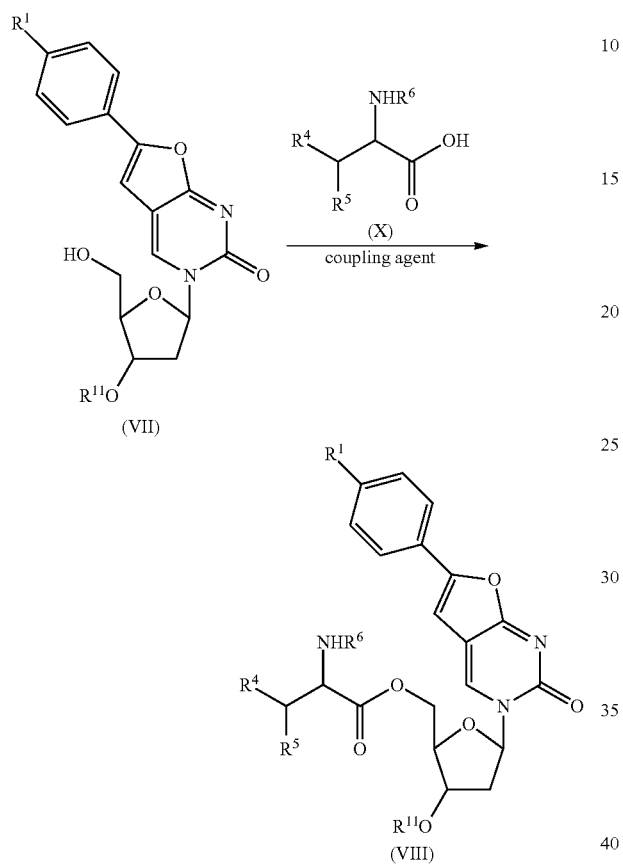

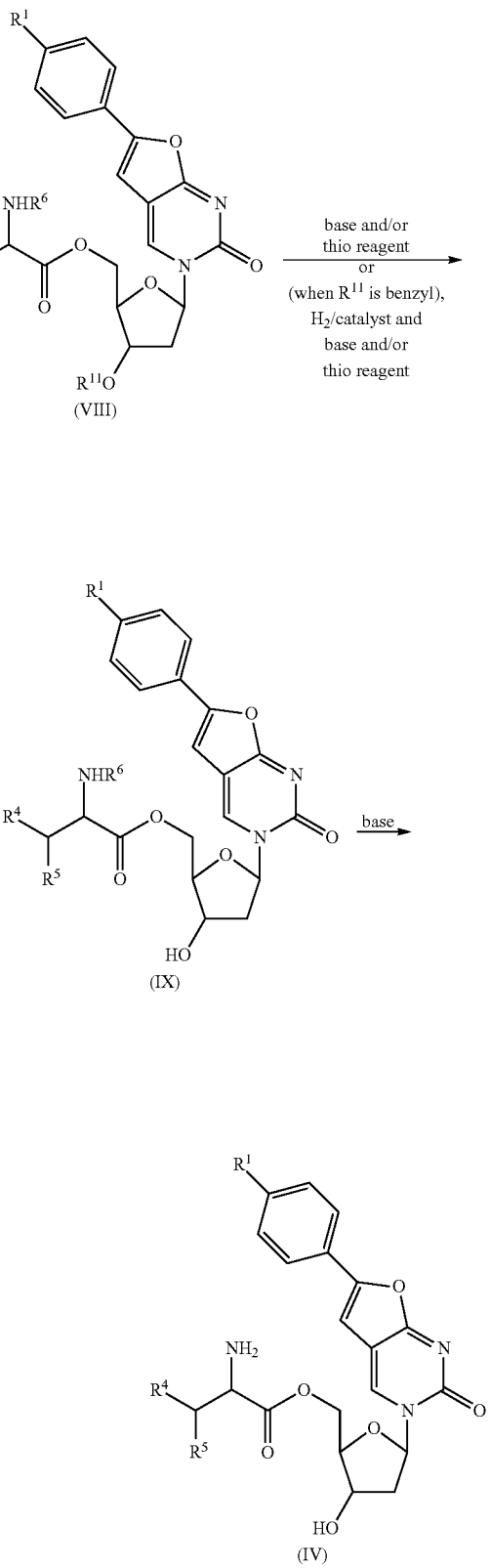

comprising the esterification of primary hydroxyl group in intermediate of Formula (VII) with a protected amino acid of Formula (X), optionally in the presence of a coupling (dehydrating) agent and a base, to form the intermediate compound of Formula (VIII),
wherein
$R^4$ and $R^5$ are independently H or $C_1$-$C_2$ alkyl;
$R^6$ represents an amino acid protecting group selected from Boc, Fmoc, and Cbz; and
$R^1$ and $R^{11}$ are as described above.

Suitable protecting groups include Boc (butyloxycarbonyl, also referred to as t-Boc, or tert-butyloxycarbonyl), Fmoc (9-fluorenylmethoxycarbonyl) and Cbz (carboxybenzyl) or other conventional protecting groups well known in the art. Suitable coupling (dehydrating) agents include dicyclohexylcarbodiimide (DCC), EDC, CDI, HOBT, $PPh_3$/DEAD, $PPh_3$/DIAD and the like. Suitable bases include DMAP and the like. Suitable solvents are non-protic polar solvents such as THF and the like.

The process is carried out at a temperature sufficient to promote reaction, generally from about 0° C. to about 50° C., preferably at ambient (room) temperature.

In yet another aspect of the invention, there is provided a process for the synthesis of the compound of Formula (IX) from the compound of Formula (VIII):

comprising the deprotection of the secondary hydroxyl group $R^{11}$ and amino acid protecting group ($R^6$) present in the intermediate of Formula (VIII), to provide the compound Formula (IV), wherein $R^1$, $R^4$, $R^5$ and $R^{11}$ are as described above.

Deprotection of the $R^6$ moiety and the $R^{11}$ group, when is $R^{11}$ is $C_1$-$C_6$ alkanoyl, halogen substituted alkanoyl, or optionally substituted aroyl, is facilitated by a suitable mild base, and/or thio reagent.

When $R^{11}$ is optionally substituted benzyl, Cbz or diphenylmethyl, deprotection is accomplished by catalytic hydrogenation.

Suitable mild bases useful in this step are bases such as pyrrole, piperidine, morpholine, DBU, sodium carbonate; thio reagents, such as thiourea, mercaptans, or combinations thereof.

Suitable catalysts for catalytic hydrogenation include platinum, nickel, Rhodium or palladium catalysts such as Raney Ni, Pd on C, Pt on C, Rh—C, Rh/$Al_2O_3$, and $Pt_2O$.

The hydrogenolysis deprotection reaction may be carried out in a suitable solvent such as protic solvents such as methanol, ethanol, formic acid and acetic acid, or inert solvents such as DMF(N,N-dimethylformamide), NMP(N-methylpyrrolidine), DMAC(N,N-dimethylacetamide), DMSO THF, 2-Me-THF, ethyl acetate, etc, or combination of the above. The reaction may be carried out under hydrogen pressures of 15 to 500 psi using standard apparatus (e.g., a Parr Shaker).

The deprotection of the $R^{11}$ can be carried out first, and the intermediate of Formula (IX) may optionally be isolated. Alternatively, the deprotection of both the $R^{11}$ and $R^6$ groups can be conducted simultaneously or in sequence without isolation of any intermediates, to provide the compound of Formula (IV) directly.

Detailed process steps and reagents, as well as preferred reaction conditions may be found in the specific examples, infra.

An embodiment of the invention is the process as described above for the synthesis of the Formula (IV), where $R^1$ is n-pentyl and $R^4$ and $R^5$ are methyl, i.e., Compound 4 and its hydrochloride salt, FV-100.

Compound 4

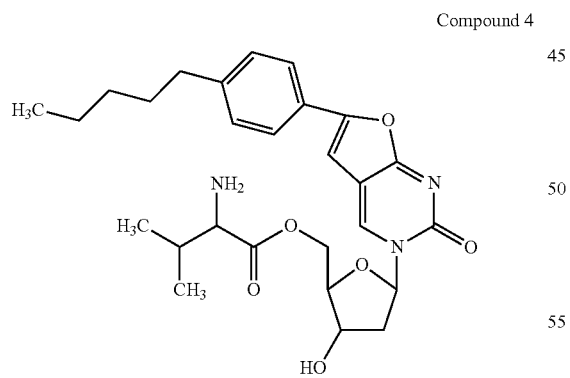

Further embodiments of the invention are the processes for the synthesis of novel intermediate compounds (Compounds 5-10) from which FV-100 is thereby produced.

Further aspects of the invention are directed to novel intermediates of Formulae (V),-(VIII). These are described as follows:

One embodiment of this aspect is the compound of Formula (V)

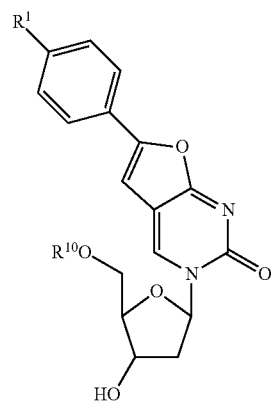

(V)

wherein $R^1$ is $C_1$-$C_6$ alkyl; and $R^{10}$ is trityl, 4,4'-dimethoxytrityl, diphenylmethylsilyl or tert-butyldiphenylsilyl.

Another embodiment of this aspect is the compound of Formula (VI)

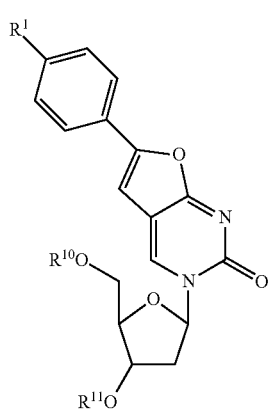

(VI)

wherein $R^1$ is $C_1$-$C_6$ alkyl;

$R^{10}$ is trityl, 4,4'-dimethoxytrityl, tert-butyldimethylsilyl, diphenylmethylsilyl or tert-butyldiphenylsilyl; and $R^{11}$ is selected from $C_1$-$C_6$ alkanoyl such as acetyl;

halogen substituted alkanoyl such as chloroacetyl, dichloroacetyl, trichloroacetyl, bromoacetyl, fluoroacetyl, difluoroacetyl, and trifluoroacetyl;

optionally substituted aroyl such as halobenzoyl and nitrobenzoyl;

optionally substituted benzyl;

Cbz; and diphenylmethyl.

In yet another embodiment of this aspect is the compound of Formula (VII)

(VII)

[Structure of Formula VII]

wherein
R¹ is $C_1$-$C_6$ alkyl; and
R¹¹ is selected from
  $C_1$-$C_6$ alkanoyl such as acetyl;
  halogen substituted alkanoyl such as chloroacetyl, dichloroacetyl, trichloroacetyl, bromoacetyl, fluoroacetyl, difluoroacetyl, and trifluoroacetyl;
  optionally substituted aroyl such as halobenzoyl and nitrobenzoyl;
  optionally substituted benzyl;
  Cbz; and
  diphenylmethyl.

In yet another embodiment of this aspect is the compound of Formula (VIII)

(VIII)

[Structure of Formula VIII]

wherein
R¹ is $C_1$-$C_6$ alkyl;
R⁴ and R⁵ are each independently H or $C_{1-2}$ alkyl;
R¹¹ is selected from
  $C_1$-$C_6$ alkanoyl such as acetyl;
  halogen substituted alkanoyl such as chloroacetyl, dichloroacetyl, trichloroacetyl, bromoacetyl, fluoroacetyl, difluoroacetyl, and trifluoroacetyl;
  optionally substituted aroyl such as halobenzoyl and nitrobenzoyl;
  optionally substituted benzyl;
  Cbz; and
  diphenylmethyl; and
R⁶ is an amino acid protecting group selected from Boc, Fmoc, and Cbz.

A further embodiments of this aspect of the invention is a novel intermediate compound selected from Compounds 5-10:

Compound 5

Compound 6

Compound 7

Compound 8

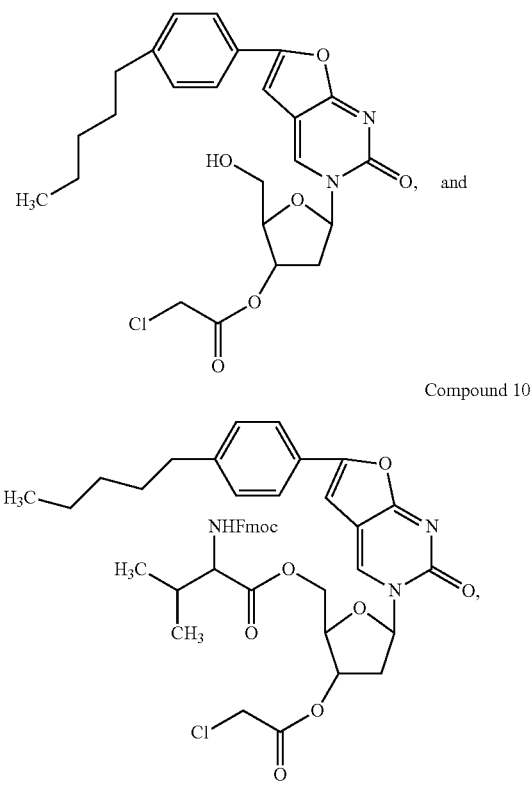

Compound 9

Compound 10

In Compounds 5-10, Tr represents trityl(triphenylmethyl);
DMTr represents 4,4'-dimethoxytrityl[bis(4-methoxyphenyl)(phenyl)methyl];
and Fmoc represents 9-fluorenylmethoxycarbonyl.

In a further aspect of the invention, there is provided a process for the purification of the hydrochloride salt of the compound of Formula (IV), where $R^1$ is n-pentyl and $R^4$ and $R^5$ are methyl, i.e., Compound 4HCl salt, FV-100, comprising the steps of 1) dissolving the crude Compound 4 hydrochloride salt in a suitable solvent to form a solution;

2) adding sufficient anti-solvent to the solution to effect formation of a solid precipitate; and 3) isolating the solid precipitate.

The precipitated solid isolated in step 3 is a purified form of the hydrochloride salt of Compound 4.

Suitable solvents for dissolving the crude compound of Formula (IV) is selected from, but not limited to aprotic polar solvents, protic solvents or mixture thereof, such as DMSO, DMF, NMP, methanol/DCM, DMF/DCM, DMSO/DCM, THF/H$_2$O, methanol/DCM/MTBE mixed solvents and the like.

An anti-solvent is a solvent in which the Compound 4 does not readily dissolve. For this purification, the anti-solvent is selected from, but not limited to less polar solvents such as alkanes, haloalkanes, ethers, esters, alcohols, and the like.

The present invention also describes polymorphic forms (I and II) of the hydrochloride salt of Compound 4, and a process for the transformation of polymorphic form (I) or a mixture of polymorphic forms (I and II) of the hydrochloride salt of Compound 4 into its polymorphic form (II), comprising the steps of 1. allowing the solid polymorphic form (I) or the mixture of polymorphic forms (I and II) of the hydrochloride salt of Compound 4 to age in a suitable solvent or solvent mixture for a sufficient period of time; and 2. isolating the resulting solids from the solvent.

The resulting solids isolated in step 2 is the hydrochloride salt of Compound 4, polymorphic form (II).

The process can be carried out with or without agitation, in the optional presence of a base.

The suitable solvent or solvent mixtures for this process include water or mixture of water and organic solvent, such as water/acetonitrile and the like.

The base can be an organic or inorganic base selected from, but not limited to sodium bicarbonate, sodium carbonate or other in-organic bases; triethylamine, diisopropylethylamine, piperidine or other organic bases. The amount of base used can vary from none to an amount sufficient to neutralize any excess acid (e.g., HCl) present in the starting material to be transformed by the process. Preferable amounts of base are from about 0.0 to about 0.1 equivalents per equivalent of starting material.

Preferably, but not exclusively, the aging can be carried out at temperatures at about or below about 100° C.

The time for the aging in step 1 is determined to be sufficient when a sample is removed from the mixture and analyzed for completeness of the transformation. Among the preferred times that are sufficient are from about 2 hours to about 4 days.

DEFINITIONS

The term "alkyl", by itself or as part of another substituent, means, unless otherwise stated, a straight or branched chain radical, which may be fully saturated, mono- or polyunsaturated and can include di- and multivalent radicals, having the number of carbon atoms designated (e.g., C1-C10 means one to ten carbons). Examples of saturated hydrocarbon radicals include, but are not limited to, groups such as methyl, ethyl, n-propyl, iso-propyl, n-butyl, iso-butyl, t-butyl, sec-butyl, n-pentyl, n-hexyl, n-heptyl, and n-octyl.

The terms "halo" or "halogen", by themselves or as part of another substituent, mean, unless otherwise stated, a fluorine, chlorine, bromine, or iodine atom.

The term "aryl" mean, unless otherwise stated, a substituted or unsubstituted polyunsaturated, aromatic, hydrocarbon substituent, which can be a single ring, or multiple rings (preferably from 1 to 3 rings), which are fused together or linked covalently.

The term "alkanoyl" by itself or as part of another substituent, means, unless otherwise stated an alkyl-C(=O)— group where the point of attachment of the group to the rest of the molecule as on the carbon atom bearing the carbonyl (=O) moiety. The alkyl group may be optionally substituted. Such group include acetyl [CH$_3$C(=O)—], chloroacetyl ClCH$_2$C(=O)—]propanoyl[CH$_3$CH$_2$(C=O)—], isobutanoyl[(CH$_3$)$_2$CH(C=O)—], hexanoyl[CH$_3$(CH$_2$)$_3$CH$_2$(C=O)—], and the like.

The term "aroyl" by itself or as part of another substituent, means, unless otherwise stated an aryl-C(=O)— group where the point of attachment of the group to the rest of the molecule as on the carbon atom bearing the carbonyl (=O) moiety. The aryl group may be optionally substituted. Such groups include benzoyl, 4-chlorobenzoyl, naphthoyl and the like.

The term "acyl" by itself or as part of another substituent, means ether aroyl or alkanoyl as defined above.

The term "bulky silyl group" means a silyl group in which is substituted one or more times the remaining three positions with alkyl groups, particularly branched alkyl groups. Such groups include tert-butyldimethylsilyl[(Me)₂(t-Bu)Si—], diphenylmethylsilyl[(Ph)₂(Me)Si—], and tert-butyldiphenylsilyl[(Ph)₂(t-Bu)Si—].

The term "non-polar amino acid" means a neutral amino acid of Formula (XI):

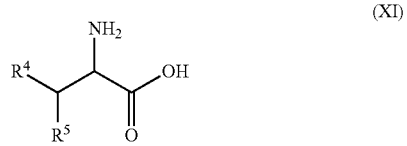

in which $R^4$ and $R^5$ are each independently H or $C_{1-2}$ alkyl.

Each compound of the present invention may be a pure stereoisomer coupled at each of its chiral centers or may be inverted at one or more of its chiral centers I may be a single stereoisomer or a mixture of two or more stereoisomers. If it is a mixture the ratio may or may not be equimolar. Preferably the compound is a single stereoisomer. The compound may be in either enantiomeric form, i.e., it may be either the D or L (alternately designated R or S) enantiomer either as a single stereoisomer or as a mixture of the two enantiomers. More preferably the compounds have a stereochemistry resembling natural deoxy nucleosides derived from β-D-2-deoxyribose. However other enantiomers, particularly the L enantiomers may be employed.

The term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "polymorphs" refers to any polymorphic forms that can exist in compounds described herein, as recognized by one of ordinary skill in the art. As known in the art, polymorphism is an ability of a compound to crystallize as more than one distinct crystalline or "polymorphic" species. The importance of polymorphs in the pharmaceutical industry and general methods and techniques for obtaining polymorphs, such as slurrying, re-slurrying and aging (ripening), are described in the review article, "Crystal Polymorphism in Chemical Process Development", *Annual Review of Chemical and Biomolecular Engineering*, Vol. 2: 259-280 (July 2011), incorporated by reference herein. A "polymorph" is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds. Polymorphs can be characterized by distinct physical properties, such as X-Ray Powder Diffraction (or XRPD) patterns.

ABBREVIATIONS AND ACRONYMS

Ac acetyl
atm atmosphere
Boc butyloxycarbonyl
Cbz carboxybenzyl
CbzCl benzyl chloroformate
CDCl₃ deuterochloroform
CDI 1,1'-carbonyldiimidazole
d doublet (NMR)
DCC dicyclohexylcarbodiimide
DCM dichloromethane
DBU 1,8-Diazabicyclo[5.4.0]undec-7-ene
dd doublet of doublets(NMR)
DEAD diethyl azodicarboxylate
DIAD diisopropyl azodicarboxylate
DMAP 4-methylaminopyridine
DMSO dimethylsulfoxide
DMSO-d₆ hexadeuterodimethylsulfoxide
DMT-Cl 4,4'-dimethoxytrityl chloride
DMTr 4,4'-dimethoxytrityl
EA ethyl acetate
EDC 1-ethyl-3-(3-dimethyllaminopropyl) carbodiimide
ESI-MS Electrospray ionization Mass Spectrometry
Et ethyl
Fmoc 9-fluorenylmethoxycarbonyl
g gram(s)
¹H NMR proton nuclear resonance spectroscopy
h hour(s)
HOAc acetic acid
HOBT 1-hydroxybenzotriazole
Hz hertz
IPA isopropanol
J coupling constant (NMR)
kg kilogram
L liter(s)
m multiplet (NMR)
Me methyl
MHz megahertz
mL milliliter
mmol millimole
mol mol
mp melting point
MTBE methyl tert-butyl ether
NMP N-methyl-2-pyrrolidone
PHN post herpetic neuralgia
Pr propyl
Rf retention factor (TLC)
rt room temperature
s singlet
t triplet
TBAF tetra-n-butylammonium fluoride
TFA trifluoroacetic acid
THF tetrahydrofuran
TLC thin layer chromatography
tosyl p-toluenesulfonyl
Tr trityl (triphenylmethyl)
VZV varicella zoster virus
XRPD X-ray powder diffraction

EXPERIMENTAL EXAMPLES

The specific examples herein described are not intended to be exhaustive or to limit the invention to the precise reagents, reaction steps or conditions disclosed. They have been chosen and described to explain the principles of the invention, and its application and practical use to thereby enable others skilled in the art to understand its teachings.

General Methods

Proton NMR (¹H NMR) spectra were recorded on a Varian Mercury spectrometer at 400 MHz, using tetramethylsilane as an internal standard. Chemical shifts (δ) are reported in parts per million (ppm) and the coupling constants (J) are given in hertz. Signal splitting patterns are described as singlet (s), doublet (d), triplet (t), quartet (q), broad signal (br), doublet of doublet (dd), doublet of triplet (dt), or multiplet (m).

Thin Layer Chromatography (TLC) was carried out on silica gel GF254.

Melting points (mp) were determined using an XT4A digital melting point apparatus.

Optical rotations were determined by SGW-1 automatic polarimeter and expressed as $[\alpha]^D_{20}$.

Electrospray Ionization Mass Spectra (ESI-MS) were obtained on an Agilent 1100 LC/MSD instrument.

The following non-limiting specific examples illustrate embodiments of the invention.

Example 1

Preparation of 3-((2R,4S,5R)-5-(Triphenylmethoxy)methyl)-4-hydroxy-tetrahydrofuran-2-yl)-6-(4-pentylphenyl)furo[2,3-d]pyrimidin-2(3H)-one

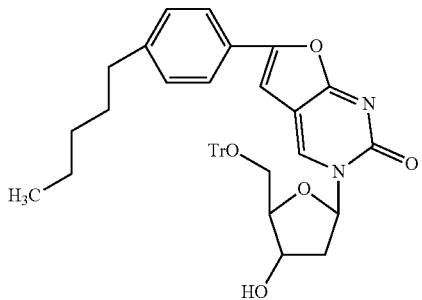

A 5 L 3-neck flask was charged with 500 g (1.25 mol) of 3-((2R,4S,5R)-(4-hydroxy-5-(hydroxymethyl)-tetrahydrofuran-2-yl)-6-(4-pentylphenyl)furo[2,3-d]pyrimidin-2(3H)-one, and 2500 mL of pyridine. The mixture was stirred and to it at rt was added dropwise 508 g (1.5 mmol) trityl chloride dissolved in 120 mL of dichloromethane solution. After the addition, the mixture was stirred for 3-5 h at rt. The mixture was then quenched with 50 mL of water. The mixture was concentrated to dryness. The residue was redissolved with 5000 mL of dichloromethane. The organic solution was washed with brine, concentrated and used directly in the next step.

Example 2

Preparation of 3-((2R,4S,5R)-5-((bis(4-Methoxyphenyl)(phenyl)methoxy)methyl)-4-hydroxy-tetrahydrofuran-2-yl)-6-(4-pentylphenyl)furo[2,3-d]pyrimidin-2(3H)-one

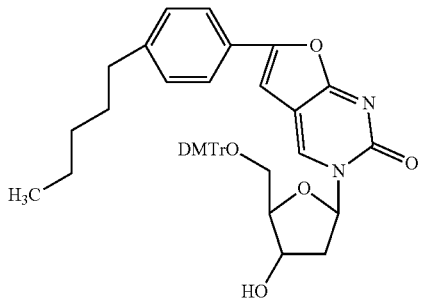

A 50 L reactor was charged with 2.8 kg (7.03 mol) of 3-((2R,4S,5R)-4-hydroxy-5-(hydroxymethyl)-tetrahydrofuran-2-yl)-6-(4-pentylphenyl)furo[2,3-d]pyrimidin-2(3H)-one, 2.8 kg (35.4 mol) of pyridine and 22.4 kg of dichloromethane. The mixture was stirred and to it was added 2.86 kg (8.44 mol) 4,4'-dimethoxyltritylchloride (DMT-Cl) in 14.9 kg dichloromethane at room temperature (rt). After addition, the mixture was stirred for 0.5 h at rt. The mixture was filtered and the filtrate was washed with brine. The filtrate contained the desired product which was used directly in the next step.

Analysis was carried out on an isolated sample:

$^1$H NMR (400 MHz, DMSO-$d_6$) δ 8.70 (s, 1H), 8.27 (s, 1H), 7.60 (d, J=8 Hz, 2H), 7.40-7.23 (m, 9H), 6.92-6.89 (m, 4H), 6.89 (s, 1H), 6.14 (dd, J=6.6 Hz, 4.4 Hz, 1H), 4.43 (d, J=6.8 Hz, 1H), 4.02 (m, 1H), 3.71 (s, 3H), 3.69 (s, 3H), 3.42-3.29 (m, 2H), 2.82 (dd, J=14.2 Hz, 7.6 Hz, 2H), 2.61 (t, J=7.6 Hz, 2H), 2.48-2.25 (m, 2H), 1.58 (m, 2H), 1.33-1.06 (m, 4H), 1.07 (t, J=7 Hz, 3H)

Example 3

Preparation of 3-((2R,4S,5R)-(5-((tert-butyldimethylsilyloxy)methyl)-4-hydroxy-tetrahydrofuran-2-yl)-6-(4-pentylphenyl)furo[2,3-d]pyrimidin-2(3H)-one

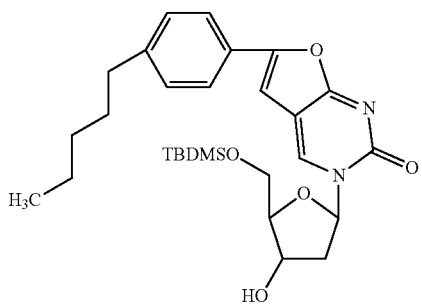 [SMILES: CCCCCc1ccc(-c2cc3cn(C4CC(O)C(CO[Si](C)(C)C(C)(C)C)O4)c(=O)nc3o2)cc1]

To a 25 mL flask was added 398 mg (1.0 mmol) of 3-((2R, 4S,5R) (4-hydroxy-5-(hydroxymethyl)-tetrahydrofuran-2-yl)-6-(4-pentylphenyl)furo[2,3-d]pyrimidin-2(3H)-one, 450 mg (3.0 mmol) of tert-butyldimethylsilylchloride, 204 mg (3.0 mmol) of imidazole and 5 mL of DMF. The mixture was stirred at rt for 2 h and monitored by TLC TLC: eluant:petroleum ether/ethyl acetate=1:1;

3-((2R,4S,5R)-(4-hydroxy-5-(hydroxymethyl)-tetrahydrofuran-2-yl)-6-(4-pentylphenyl)furo[2,3-d]pyrimidin-2(3H)-one:

$R_f$=0;

3-((2R,4S,5R)-(5-((tert-butyldimethylsilyloxy)methyl)-4-hydroxy-tetrahydrofuran-2-yl)-6-(4-pentylphenyl)furo[2,3-d]pyrimidin-2(3H)-one:

$R_f$=0.25

The mixture was poured into water. The solution was extracted by EtOAc. The organic layer was washed by water twice, dried by $Na_2SO_4$ and concentrated under vacuum. The crude product was purified by column chromatograph (eluant: from petroleum ether/ethyl acetate=1:1 to ethyl acetate) to afford product 394 mg as white solid, 77% yield.

A sample was analyzed by $^1$H NMR (400 MHz, $CDCl_3$): δ 8.72 (s, 1H), 7.65 (d, J=8.0 Hz, 2H), 7.23 (d, J=8.0 Hz, 2H), 6.59 (s, 1H), 6.46 (t, J=6.0 Hz, 1H), 4.52-4.49 (m, 1H), 4.23 (d, J=3.2 Hz, 1H), 4.04 (dd, J=12 Hz, J=2.4 Hz, 1H), 3.91 (dd, J=12 Hz, J=2.4 Hz, 1H), 3.62 (bs, 1H), 2.87-2.82 (m, 1H), 2.61 (t, J=7.6 Hz, 2H), 2.24-2.17 (m, 1H), 1.64-1.58 (m, 2H), 1.35-1.28 (m, 4H), 0.90 (s, 12H), 0.14 (s, 3H), 0.10 (s, 3H).

Example 4

Preparation of (2R,3S,5R)-5-(2-Oxo-6-(4-pentylphenyl)furo[2,3-d]pyrimidin-3(2H)-yl)-2-(bis(4-methoxyphenyl)(phenyl)methoxy)methyl)-tetrahydrofuran-3-yl-2-chloroacetate

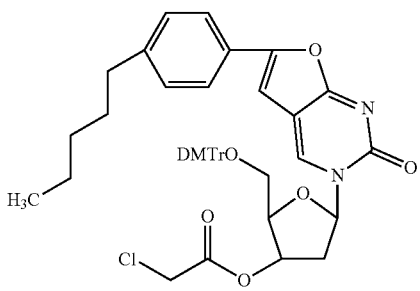

To the above filtrate from Example 2 was added 1.99 kg (16.29 mol) of N,N'-dimethylpyridine (DMAP), and 1.83 kg (16.29 mol) chloroacetyl chloride at rt. The reaction mixture was stirred until completion of reaction as monitored by TLC:

TLC eluant: DCM/methanol=15:1
3-((2R,4S,5R)-5-((bis(4-methoxyphenyl)(phenyl)methoxy)methyl)-4-hydroxy-tetrahydrofuran-2-yl)-6-(4-pentylphenyl)furo[2,3-d]pyrimidin-2(3H)-one:
$R_f$=0.32;
(2R,3S,5R)-5-(2-oxo-6-(4-pentylphenyl)furo[2,3-d]pyrimidin-3(2H)-yl)-2-(bis(4-methoxyphenyl)(phenyl)methoxy)methyl)-tetrahydrofuran-3-yl-2-chloroacetate:
$R_f$=0.75.

The mixture was concentrated to about ¼ of the original volume. The residue containing the desired product was used directly in the next step.

A sample was analyzed by $^1$H NMR: (400 MHz, CDCl$_3$) δ 8.70 (s, 1H), 7.60 (d, J=8.4 Hz, 2H), 7.40-7.23 (m, 11H), 6.87-6.83 (m, 4H), 6.46 (t, J=6 Hz, 1H), 5.83 (s, 1H), 5.59-5.56 (m, 1H), 4.31 (dd, J=6.2 Hz, 2.8 Hz, 1H), 4.14 (d, J=2.4 Hz, 2H), 3.75 (s, 3H), 3.74 (s, 3H), 3.58-3.49 (m, 2H), 2.94-2.88 (m, 1H), 2.64 (t, J=7.6 Hz, 2H), 2.51-2.46 (m, 1H), 1.67-1.59 (m, 2H), 1.37-1.25 (m, 4H), 0.89 (t, J=7.2 Hz, 3H)

Example 5

Preparation of (2R,3S,5R)-5-(2-Oxo-6-(4-pentylphenyl)furo[2,3-d]pyrimidin-3(2H)-yl)-2-(tert-butyldimethylsilyloxymethyl)-tetrahydrofuran-3-yl 2-chloroacetate

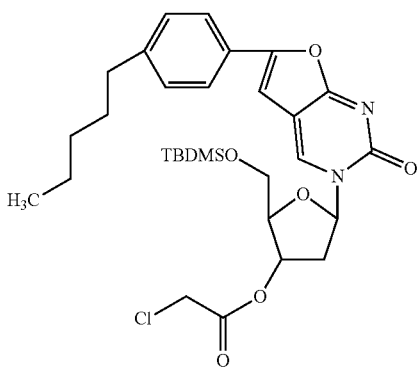 [SMILES: CCCCCc1ccc(-c2cc3cn(C4CC(OC(=O)CCl)C(CO[Si](C)(C)C(C)(C)C)O4)c(=O)nc3o2)cc1]

To a 25 mL flask was added 102 mg (0.2 mmol) of 3-(5-((tert-butyldimethyl silyloxy)methyl)-4-hydroxy-tetrahydrofuran-2-yl)-6-(4-pentylphenyl)furo[2,3-d]pyrimidin-2(3H)-one, 48 mg (0.4 mmol) of DMAP, and 5 mL of DCM. 30 μl (0.4 mmol) of chloroacetyl chloride was added dropwise. The mixture was stirred at rt for 1 h.

TLC: eluant:petroleum ether/ethyl acetate=1:1;
3-((2R,4S,5R5-((tert-butyldimethylsilyloxy)methyl)-4-hydroxy-tetrahydrofuran-2-yl)-6-(4-pentylphenyl)furo[2,3-d]pyrimidin-2(3H)-one:
$R_f$=0.10;
(2R,3S,5R)-5-(2-oxo-6-(4-pentylphenyl)furo[2,3-d]pyrimidin-3(2H)-yl)-2-(tert-butyldimethylsilyloxymethyl)-tetrahydrofuran-3-yl 2-chloroacetate:
$R_f$=0.40.

The solution was concentrated under vacuum. The crude product was purified by column chromatograph (eluant:petroleum ether/ethyl acetate from 3:1 to 2:1) to afford product 70 mg as white solid, 60% yield.

A sample was analyzed by $^1$H NMR (400 MHz, CDCl$_3$): δ 8.56 (s, 1H), 7.68 (d, J=8.4 Hz, 2H), 7.25 (d, J=8.4 Hz, 2H), 6.58 (s, 1H), 6.46 (t, J=6.0 Hz, 1H), 5.36 (d, J=6.4 Hz, 1H), 4.31 (d, J=1.6 Hz, 1H), 4.12 (s, 2H), 4.03 (dd, J=11.6 Hz, J=2.4 Hz, 1H), 3.95 (dd, J=12 Hz, J=2.4 Hz, 1H), 2.96-2.91 (m, 1H), 2.63 (t, J=7.6 Hz, 2H), 2.21-2.14 (m, 1H), 1.67-1.59 (m, 3H), 1.35-1.31 (m, 3H), 1.24 (s, 3H), 0.89 (s, 9H), 0.14 (s, 3H), 0.12 (s, 3H).

Example 6

Preparation of (2R,3S,5R)-5-(2-Oxo-6-(4-pentylphenyl)furo[2,3-d]pyrimidin-3(2H)-yl)-2-((tert-butyldimethylsilyloxy)methyl)-tetrahydrofuran-3-yl Benzyl Carbonate

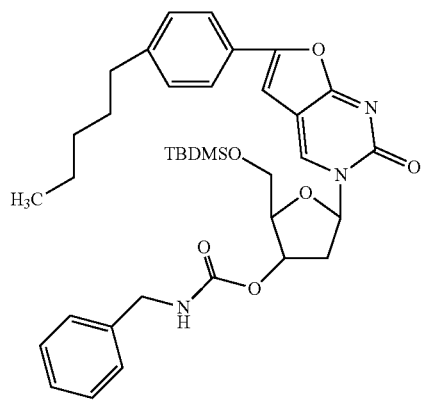 [SMILES: CCCCCc1ccc(-c2cc3cn(C4CC(OC(=O)NCc5ccccc5)C(CO[Si](C)(C)C(C)(C)C)O4)c(=O)nc3o2)cc1]

To a 25 mL flask was added 256 mg (0.5 mmol) of 3-(5-((tert-butyldimethyl silyloxy)methyl)-4-hydroxy-tetrahydrofuran-2-yl)-6-(4-pentylphenyl)furo[2,3-d]pyrimidin-2(3H)-one, 488 mg (4.0 mmol) of DMAP, and 10 mL of DCM. 0.57 mL (4.0 mmol) of CbzCl was added dropwise. The mixture was stirred at rt for 6 h.

TLC: eluant:petroleum ether/ethyl acetate=2:1;
3-((2R,4S,5R)-5-((tert-butyldimethylsilyloxy)methyl)-4-hydroxy-tetrahydrofuran-2-yl)-6-(4-pentylphenyl)furo[2,3-d]pyrimidin-2(3H)-one:
$R_f$=0.10;
(2R,3S,5R)-5-(2-oxo-6-(4-pentylphenyl)furo[2,3-d]pyrimidin-3(2H)-yl)-2-((tert-butyldimethylsilyloxy)methyl)-tetrahydrofuran-3-ylbenzyl carbonate:
$R_f$=0.50.

The solution was concentrated under vacuum. The crude product was purified by column chromatography (eluant: petroleum ether/ethyl acetate=3:1) to afford 258 mg product as white solid, 80% yield.

A sample was analyzed by $^1$H NMR (400 MHz, CDCl$_3$): δ 8.55 (s, 1H), 7.67 (d, J=8.0 Hz, 2H), 7.40-7.31 (m, 5H), 7.25 (d, J=8.0 Hz, 2H), 6.57 (s, 1H), 6.43 (t, J=6.0 Hz, 1H), 5.18 (s, 2H), 4.35 (d, J=2.0 Hz, 1H), 4.02 (d, J=12.0 Hz, 1H), 3.91 (d, J=12.0 Hz, 1H), 2.96-2.91 (m, 1H), 2.63 (t, J=7.6 Hz, 2H), 2.21-2.17 (m, 1H), 1.66-1.61 (m, 2H), 1.34-1.30 (m, 4H), 0.89 (s, 12H), 0.13 (s, 3H), 0.10 (s, 3H).

Example 7

Preparation of (2R,3S,5R)-5-(2-Oxo-6-(4-pentylphenyl)furo[2,3-d]pyrimidin-3(2H)-yl)-2-(hydroxymethyl)-tetrahydrofuran-3-yl-2-chloroacetate

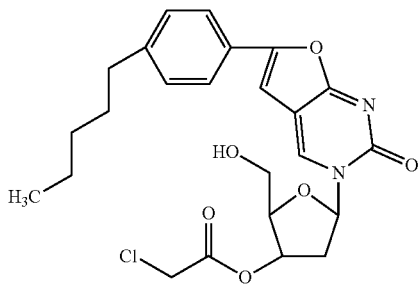 [SMILES: CCCCCc1ccc(-c2cc3cn(C4CC(OC(=O)CCl)C(CO)O4)c(=O)nc3o2)cc1]

To the residue from Example 4 was added 17.3 kg (288.5 mol) of acetic acid. Under stirring, 4.3 kg of water was added and the mixture was stirred at 30-35° C. for 4-6 h.

The reaction mixture was stirred until completion of reaction as monitored by TLC.

TLC: eluant: DCM/ethyl acetate=2:1;

(2R,3S,5R)-5-(2-oxo-6-(4-pentylphenyl)furo[2,3-d]pyrimidin-3(2H)-yl)-2-(bis(4-methoxyphenyl)(phenyl)methoxy)methyl)-tetrahydrofuran-3-yl-2-chloroacetate:

R$_f$=0.76;

(2R,3S,5R)-5-(2-oxo-6-(4-pentylphenyl)furo[2,3-d]pyrimidin-3(2H)-yl)-2-(hydroxymethyl)-tetrahydrofuran-3-yl-2-chloroacetate:

R$_f$=0.38).

The mixture was filtered and the filter cake was washed with 40 mL of dichloromethane 3 times to give the desired product.

$^1$H NMR (400 MHz, DMSO-d$_6$): δ 8.79 (s, 1H), 7.75 (d, J=8.4 Hz, 2H), 7.33 (d, J=8.4 Hz, 2H), 7.24 (s, 1H), 6.24 (t, J=6 Hz, 1H), 5.35 (d, J=6 Hz, 1H), 4.49 (d, J=2 Hz, 2H), 4.25 (d, J=1.6 Hz, 1H), 3.73-3.68 (m, 2H), 2.67-2.60 (m, 3H), 2.51-2.31 (m, 1H), 1.59 (m, 2H), 1.32-1.26 (m, 4H), 0.87 (t, J=6.8 Hz, 3H)

Example 8

Preparation of (2R,3S,5R)-5-(2-Oxo-6-(4-pentylphenyl)furo[2,3-d]pyrimidin-3(2H)-yl) 2-(hydroxymethyl)-tetrahydrofuran-3-yl-2-chloroacetate

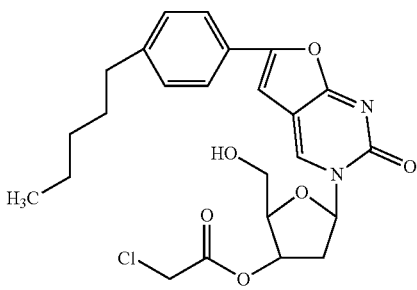 [SMILES: CCCCCc1ccc(-c2cc3cn(C4CC(OC(=O)CCl)C(CO)O4)c(=O)nc3o2)cc1]

The residue from Example 4 (13 g, 16.7 mmol) was dissolved in 45 mL of 5% of trifluoroacetic acid/dichloromethane solution. The mixture was stirred for 2 h at rt. Triethylamine (4.5 mL) was added to neutralize to pH=7. The mixture was filtered to give the desired compound.

Example 9

Preparation of (2R,3S,5R)-5-(2-Oxo-6-(4-pentylphenyl)furo[2,3-d]pyrimidin-3(2H)-yl) 2-(hydroxymethyl)-tetrahydrofuran-3-yl-2-chloroacetate

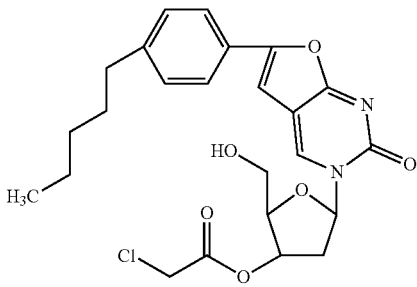 [SMILES: CCCCCc1ccc(-c2cc3cn(C4CC(OC(=O)CCl)C(CO)O4)c(=O)nc3o2)cc1]

To a 10 mL flask was added 40 mg (0.2 mmol) of (2R,3S,5R)-5-(2-oxo-6-(4-pentylphenyl)furo[2,3-d]pyrimidin-3(2H)-yl)-2-((tert-butyldimethylsilyloxy)methyl)-tetrahydrofuran-3-ylbenzyl carbonate, 2 mL of EtOAc, 2 mL of EtOH and 0.5 mL of 37% aqueous HCl.

The mixture was stirred at rt for about 0.5 h until completion of reaction as monitored by TLC.

TLC: eluant:petroleum ether/THF=2:1;

(2R,3S,5R)-5-(2-oxo-6-(4-pentylphenyl)furo[2,3-d]pyrimidin-3(2H)-yl)-2-((tert-butyldimethylsilyloxy)methyl)-tetrahydrofuran-3-ylbenzyl carbonate:

R$_f$=0.80;

(2R,3S,5R)-5-(2-oxo-6-(4-pentylphenyl)furo[2,3-d]pyrimidin-3(2H)-yl)-2-(hydroxymethyl)-tetrahydrofuran-3-yl-2-chloroacetate:

R$_f$=0.30.

The precipitate was filtered and washed with 2 mL of DCM to afford 20 mg of product as white solid.

Example 10

Preparation of (2R,3S,5R)-5-(2-Oxo-6-(4-pentylphenyl)furo[2,3-d]pyrimidin-3(2H)-yl)-2-(hydroxymethyl)tetrahydrofuran-3-yl Benzyl Carbonate

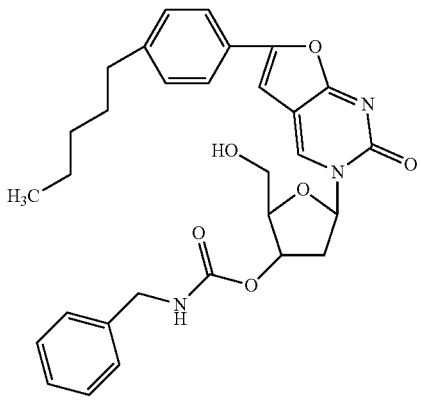 [SMILES: CCCCCc1ccc(-c2cc3cn(C4CC(OC(=O)NCc5ccccc5)C(CO)O4)c(=O)nc3o2)cc1]

To a 10 mL flask was added 20 mg (0.2 mmol) of (2R,3S,5R)-5-(2-oxo-6-(4-pentylphenyl)furo[2,3-d]pyrimidin-3(2H)-yl)-2-((tert-butyldimethylsilyloxy)methyl)-tetrahydrofuran-3-yl benzyl carbonate, 2 mL of EtOAc, 2 mL of EtOH and 0.5 mL of 37% aqueous HCl. The mixture was stirred at rt for 0.5 h.

TLC: eluant:petroleum ether/THF=2:1;

(2R,3S,5R)-5-(2-oxo-6-(4-pentylphenyl)furo[2,3-d]pyrimidin-3(2H)-yl)-2-((tert-butyldimethylsilyloxy)methyl)-tetrahydrofuran-3-yl benzyl carbonate:

$R_f$=0.80

(2R,3S,5R)-5-(2-oxo-6-(4-pentylphenyl)furo[2,3-d]pyrimidin-3(2H)-yl)-2-(hydroxymethyl)tetrahydrofuran-3-yl benzyl carbonate:

$R_f$=0.30.

The precipitate was filtered and washed by water to afford product 14 mg as white solid, 80% yield.

The structure of an isolated sample was confirmed by proton NMR:

$^1$H NMR (400 MHz, d$_4$-MeOH): δ 8.88 (s, 1H), 7.73 (d, J=8.0 Hz, 2H), 7.41-7.34 (m, 5H), 7.30 (d, J=8.0 Hz, 2H), 7.02 (s, 1H), 6.34 (t, J=6.0 Hz, 1H), 5.26 (d, J=6.4 Hz, 1H), 5.19 (s, 2H), 4.34 (d, J=2.0 Hz, 1H), 3.91 (d, J=12.0 Hz, 1H), 3.84 (d, J=12.0 Hz, 1H), 2.85-2.80 (m, 1H), 2.66 (t, J=8.0 Hz, 2H), 2.38-2.31 (m, 1H), 1.71-1.61 (m, 2H), 1.34-1.30 (m, 4H).

Example 11

Preparation of (S)-((2R,3S,5R)-3-(2-Chloroacetoxy)-5-(2-oxo-6-(4-pentylphenyl)furo[2,3-d]pyrimidin-3(2H)-yl)-tetrahydrofuran-2-yl)methyl 2-(((9H-fluoren-9-yl)methoxy)carbonylamino)-3-methylbutanoate

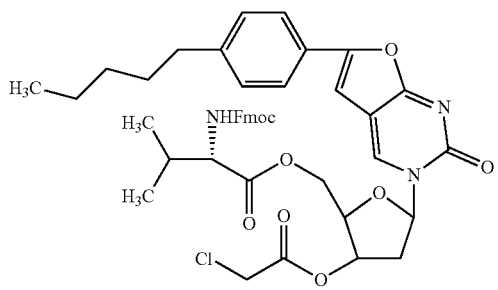

To a 250 mL 3-necked flask was added 14 g (29.5 mmol) of 2-(hydroxymethyl)-5-(2-oxo-6-(4-pentylphenyl)furo[2,3-d]pyrimidin-3 (2H)-yl)-tetrahydrofuran-3-yl-2-chloroacetate, 13.8 g (40.7 mmol) of Fmoc-L-valine, 9.09 g (44 mmol) of N,N'-dicyclohexylcarbodimide (DCC), 0.108 g (0.88 mmol) of DMAP and 70 mL of THF. The mixture was stirred at rt until completion of reaction, as monitored by TLC (approximately 2 h), and was then filtered.

TLC: eluant: DCM/ethyl acetate=2:1;

2-(hydroxymethyl)-5-(2-oxo-6-(4-pentylphenyl)furo[2,3-d]pyrimidin-3(2H)-yl)-tetrahydrofuran-3-yl-2-chloroacetate:

$R_f$=0.38;

(S)-((2R,3S,5R)-3-(2-chloroacetoxy)-5-(2-oxo-6-(4-pentylphenyl)furo[2,3-d]pyrimidin-3 (2H)-yl)-tetrahydrofuran-2-yl)methyl 2-(((9H-fluoren-9-yl)methoxy)carbonylamino)-3-methylbutanoate:

$R_f$=0.75.

The filter cake was washed with 30 mL of dichloromethane. The filtrate was concentrated under reduced pressure. The residue contained the desired product which was used directly in the next step (Example 14).

The structure of an isolated sample was confirmed by proton NMR:

$^1$H NMR (400 MHz, CDCl$_3$): δ 8.25 (s, 1H), 7.74 (d, J=7.6 Hz, 2H), 7.56-7.52 (m, 4H), 7.40 (m, 2H), 7.27 (m, 3H), 7.12 (d, J=7.6 Hz, 2H), 6.77 (s, 1H), 6.42-6.39 (m, 1H), 5.37 (d, J=6.8 Hz, 1H), 5.29-5.27 (m, 1H), 4.68 (d, J=10.4 Hz, 1H), 4.45=4.37 (m, 4H), 4.23-4.16 (m, 2H), 4.13 (s, 1H), 3.00-2.95 (m, 1H), 2.60 (t, J=7.6 Hz, 2H), 2.21-2.12 (m, 2H), 1.63-1.59 (m, 2H), 1.34-1.33 (m, 4H), 1.00-0.97 (m, 6H), 0.90 (t, J=6.8 Hz, 3H)

Example 12

(S)-((2R,3S,5R)-3-(2-Chloroacetoxy)-5-(2-oxo-6-(4-pentylphenyl)furo[2,3-d]pyrimidin-3(2H)-yl)-tetrahydrofuran-2-yl)methyl 2-(((9H-fluoren-9-yl)methoxy)carbonylamino)-3-methylbutanoate

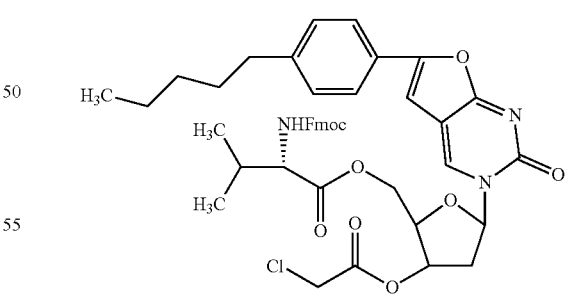

To 50 L reactor was added 2.6 kg (5.47 mol) of 2-(hydroxymethyl)-5-(2-oxo-6-(4-pentylphenyl)furo[2,3-d]pyrimidin-3 (2H)-yl)-tetrahydrofuran-3-yl-2-chloroacetate, 2.56 kg (7.54 mol) of Fmoc-L-valine, 1.69 kg (8.19 mol) of N,N'-dicyclohexylcarbodimide (DCC), 20 g (0.16 mol) of DMAP and 9.9 kg of THF. The mixture was stirred at rt until completion of reaction as monitored by TLC, (approximately 2 h), and was then filtered.

TLC: eluant: DCM/ethyl acetate=2:1;

2-(hydroxymethyl)-5-(2-oxo-6-(4-pentylphenyl)furo[2,3-d]pyrimidin-3(2H)-yl)-tetrahydrofuran-3-yl-2-chloroacetate:

R$_f$=0.38;

(S)-((2R,3S,5R)-3-(2-chloroacetoxy)-5-(2-oxo-6-(4-pentylphenyl)furo[2,3-d]pyrimidin-3 (2H)-yl)-tetrahydrofuran-2-yl)methyl 2-(((9H-fluoren-9-yl)methoxy)carbonylamino)-3-methylbutanoate:

R$_f$=0.75.

The filter cake was washed with 7.4 kg of dichloromethane. The filtrate was concentrated under reduced pressure. The residue contains the desired product which was used directly in the next step (Example 15).

Example 13

Preparation of (S)-((2R,3S,5R)-3-(Benzyloxycarbonyloxy)-5-(2-oxo-6-(4-pentylphenyl)furo[2,3-d]pyrimidin-3(2H)-yl)-tetrahydrofuran-2-yl)methyl 2-(benzyloxycarbonylamino)-3-methylbutanoate

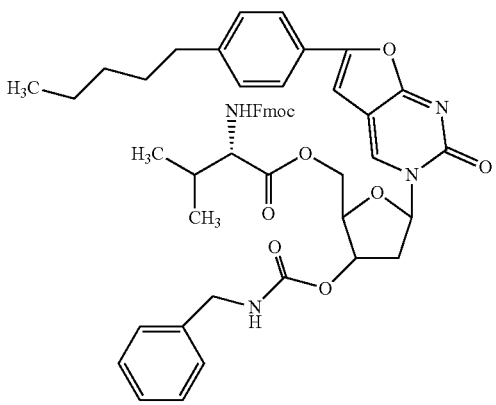

To a 25 mL flask was added 53 mg (0.1 mmol) of (2R,3S,5R)-5-(2-oxo-6-(4-pentylphenyl)furo[2,3-d]pyrimidin-3(2H)-yl)-2-((tert-butyldimethylsilyloxy)methyl)-tetrahydrofuran-3-yl benzyl carbonate, 12 mg (0.1 mmol) of DMAP, 31 mg (0.15 mmol) of DCC, 30 mg (0.12 mmol) of Cbz-Val-OH, and 5 mL of THF. The mixture was stirred at rt for 2 h.

TLC: eluant:petroleum ether/ethyl acetate=1:1;

(2R,3S,5R)-5-(2-oxo-6-(4-pentylphenyl)furo[2,3-d]pyrimidin-3(2H)-yl)-2-((tert-butyldimethylsilyloxy)methyl)-tetrahydrofuran-3-ylbenzyl carbonate:

R$_f$=0.10;

(S)-((2R,3S,5R)-3-(benzyloxycarbonyloxy)-5-(2-oxo-6-(4-pentylphenyl)furo[2,3-d]pyrimidin-3(2H)-yl)-tetrahydrofuran-2-yl)methyl 2-(benzyloxycarbonylamino)-3-methylbutanoate:

R$_f$=0.70.

The solution was concentrated under vacuum. The crude product was purified by column chromatograph (eluant:petroleum ether/ethyl acetate=2:3) to afford product 70 mg as white solid, 88% yield.

The structure of an isolated sample was confirmed by proton NMR:

$^1$H NMR (400 MHz, CDCl$_3$): δ 8.31 (s, 1H), 7.63 (d, J=8.4 Hz, 2H), 7.40-7.31 (m, 11H), 7.22 (d, J=8.4 Hz, 2H), 6.86 (s, 1H), 6.36 (t, J=6.0 Hz, 1H), 5.27 (d, J=8.8 Hz, 1H), 5.18 (s, 4H), 5.15 (d, J=12.4 Hz, 1H), 5.03 (d, J=12.4 Hz, 1H), 4.47 (m, 1H), 4.18 (m, 1H), 3.48 (m, 1H), 2.62 (t, J=7.6 Hz, 2H), 2.22-2.04 (m, 2H), 1.67-1.59 (m, 3H), 1.35-1.31 (m, 3H), 0.97 (d, J=6.8 Hz, 3H), 0.97 (d, J=6.8 Hz, 3H), 0.89 (t, J=7.6 Hz, 3H)

Example 14

Preparation of (S)-((2R,3S,5R)-(3-Hydroxy-5-(2-oxo-6-(4-pentylphenyl)furo[2,3-d]pyrimidin-3(2H)-yl)-tetrahydrofuran-2-yl))methyl 2-amino-3-methylbutanoate To the residue from Example 11 were added 35 mL of ethanol and 35 mL of dichloromethane. Under stirring, the mixture was added 4.49 g (59 mmol) of thiourea and 6.24 g (58.9 mmol) of sodium carbonate. The reaction mixture was heated to 50-60° C. for 2 h and monitored by TLC.

TLC: eluant: DCM/methanol=15:1;

(S)-((2R,3S,5R)-3-(2-chloroacetoxy)-5-(2-oxo-6-(4-pentylphenyl)furo[2,3-d]pyrimidin-3 (2H)-yl)-tetrahydrofuran-2-yl)methyl 2-(((9H-fluoren-9-yl)methoxy)carbonylamino)-3-methylbutanoate:

R$_f$=0.62;

(S)-((2R,3S,5R)-3-hydroxy-5-(2-oxo-6-(4-pentylphenyl)furo[2,3-d]pyrimidin-3(2H)-yl)-tetrahydrofuran-2-yl)methyl 2-(((9H-fluoren-9-yl)methoxy)carbonylamino)-3-methylbutanoate:

R$_f$=0.16.

Dichloromethane (70 mL) was added and stirred for 5 min. The mixture was filtered. The filtrate was washed with 70 mL of 5% brine. The organic layer was separated and charged with 15.0 g (176.1 mmol) of piperidine. The mixture was stirred at rt for 2 h and monitored by TLC for the completion of the reaction.

TLC: eluant: DCM/methanol=6:1;

(S)-((2R,3S,5R)-3-hydroxy-5-(2-oxo-6-(4-pentylphenyl)furo[2,3-d]pyrimidin-3(2H)-yl)-tetrahydrofuran-2-yl)methyl 2-(((9H-fluoren-9-yl)methoxy)carbonylamino)-3-methylbutanoate:

R$_f$=0.55;

(S)-((2R,3S,5R)-3-hydroxy-5-(2-oxo-6-(4-pentylphenyl)furo[2,3-d]pyrimidin-3(2H)-yl)-tetrahydrofuran-2-yl))methyl 2-amino-3-methylbutanoate:

R$_f$=0.24).

The reaction mixture contained the desired product which was used directly in the next step (Example 16).

Example 15

Preparation of (S)-((2R,3S,5R)-(3-Hydroxy-5-(2-oxo-6-(4-pentylphenyl)furo[2,3-d]pyrimidin-3(2H)-yl)-tetrahydrofuran-2-yl))methyl 2-amino-3-methylbutanoate

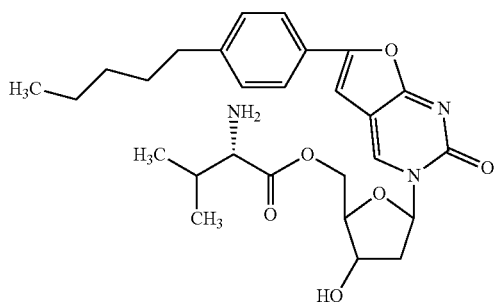 [SMILES: CCCCCc1ccc(-c2cc3cn(C4CC(O)C(COC(=O)[C@@H](N)C(C)C)O4)c(=O)nc3o2)cc1]

To the residue from Example 12 were added 5.2 kg of ethanol and 8.6 kg of dichloromethane. Under stirring, the mixture was added 0.83 g (10.9 mol) of thiourea and 1.16 kg (10.9 mol) of sodium carbonate. The reaction mixture was heated to 40-50° C. for 2 h and monitored by TLC.

TLC: eluant: DCM/methanol=15:1;

(S)-((2R,3S,5R)-3-(2-chloroacetoxy)-5-(2-oxo-6-(4-pentylphenyl)furo[2,3-d]pyrimidin-3 (2H)-yl)-tetrahydrofuran-2-yl)methyl 2-(((9H-fluoren-9-yl)methoxy)carbonylamino)-3-methylbutanoate:

$R_f$=0.62;

(S)-((2R,3S,5R)-3-hydroxy)-5-(2-oxo-6-(4-pentylphenyl)furo[2,3-d]pyrimidin-3(2H)-yl)-tetrahydrofuran-2-yl)methyl-2-(((9H-fluoren-9-yl)methoxy)carbonylamino)-3-methylbutanoate:

$R_f$=0.16

The reaction mixture was filtered and the filtrate was washed with 7.4 kg of 5% brine. The aqueous layer was extracted with 8.6 kg of dichloromethane. The organic layers were combined and charged with 2.79 kg (32.7 mol) of piperidine. The mixture was stirred at rt for 2 h and monitored by TLC.

TLC: eluant: DCM/methanol=6:1;

(S)-((2R,3S,5R)-3-hydroxy-5-(2-oxo-6-(4-pentylphenyl)furo[2,3-d]pyrimidin-3(2H)-yl)-tetrahydrofuran-2-yl)methyl 2-(((9H-fluoren-9-yl)methoxy)carbonylamino)-3-methyl butanoate:

$R_f$=0.55;

(S)-((2R,3S,5R)-(3-hydroxy-5-(2-oxo-6-(4-pentylphenyl)furo[2,3-d]pyrimidin-3(2H)-yl)-tetrahydrofuran-2-yl))methyl 2-amino-3-methylbutanoate:

$R_f$=0.24.

The reaction mixture contained the desired product which was used directly in the next step (Example 17), or was optionally evaporated to dryness.

Example 16

Preparation of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

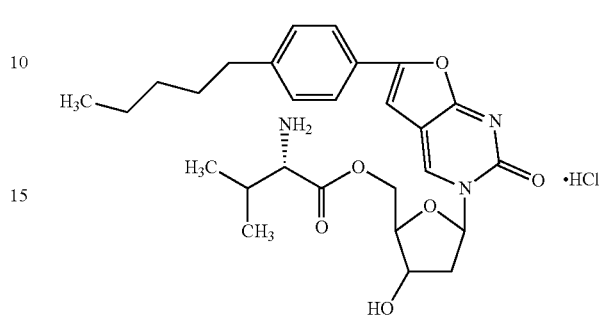

The above reaction mixture from Example 14 was cooled to 5-10° C. and was added with 20% of HCl IPA solution until pH 2~3. The mixture was stirred for additional 1 h and was filtered. The filter cake was washed with 140 mL of dichloromethane. 12.2 g of desired crude product were obtained. The overall yield from Example 11 was 71.1% and the purity was 97%. The crude product was recrystallized with methanol/dichloromethane/MTBE to give the desired pure product:

$^1$H NMR (400 MHz, DMSO-d$_6$): δ 8.58 (br s, 3H), 8.55 (s, 1H), 7.73 (d, J=8 Hz, 2H), 7.31 (d, J=8.4 Hz, 2H), 6.22 (t, J=6 Hz, 1H), 5.57 (d, J=8.8, 1H), 4.45 (m, 2H), 4.28-4.26 (m, 1H), 4.13-4.11 (m, 1H), 3.91 (d, J=4.8 Hz, 1H), 2.60 (t, J=7.6 Hz, 2H), 2.45-2.38 (m, 1H), 2.27-2.13 (m, 2H), 1.57 (t, J=7.2 Hz, 2H), 1.30-1.25 (m, 4H), 0.97 (d, J=6.8 Hz, 3H), 0.93 (d, J=6.8 Hz, 3H) (m, 6H), 0.84 (t, J=6.8 Hz, 3H).

mp: 214-218° C.

ESI-MS (M$^+$+1):499.

[α]$^D_{20}$=114~119 (C=0.5 (20° C.) in MeOH/DCM=1/1).

Example 17

Preparation of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

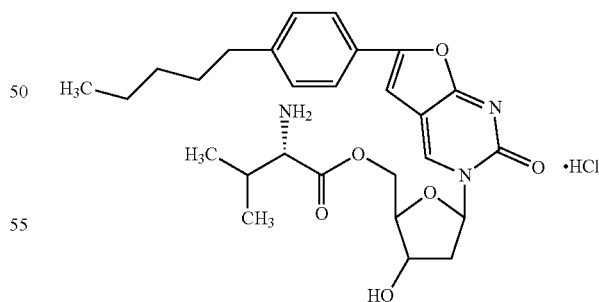

The above reaction mixture from Example 15 was cooled below 5° C. and was added with 20% of HCl IPA solution until pH 1~4. The mixture was stirred for additional 1 h and was filtered. The filter cake was washed with 34.6 kg of dichloromethane. Desired crude product was obtained. The overall yield from Example 12 was 67% and the purity was 97%. The crude product was recrystallized with methanol/dichloromethane/MTBE to give the desired pure product.

Example 18

Preparation of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate

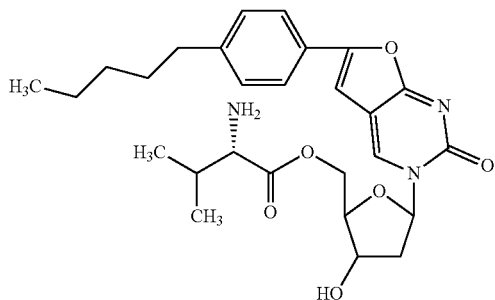 [SMILES: CCCCCc1ccc(-c2cc3cn(C4CC(O)C(COC(=O)[C@@H](N)C(C)C)O4)c(=O)nc3o2)cc1]

To a 25 mL flask was added 77 mg (0.1 mmol) of (S)-((2R,3S,5R)-3-(benzyloxycarbonyloxy)-5-(2-oxo-6-(4-pentylphenyl)furo[2,3-d]pyrimidin-3 (2H)-yl)-tetrahydrofuran-2-yl)methyl 2-(benzyloxycarbonylamino)-3-methylbutanoate, 12 mg of 10% Pd/C and 3 mL of EtOAc. The flask was transferred into a pressure reaction vessel. Then the vessel was pressurized to 260 psi with hydrogen gas. The mixture was stirred at rt for 2 h.

TLC: eluant: ethyl acetate;

(S)-((2R,3S,5R)-3-(benzyloxycarbonyloxy)-5-(2-oxo-6-(4-pentylphenyl)furo[2,3-d]pyrimidin-3(2H)-yl)-tetrahydrofuran-2-yl)methyl 2-(benzyloxycarbonylamino)-3-methylbutanoate:

$R_f$=0.70;

(S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate:

$R_f$=0.10

The solution was filtered and the crude product was concentrated under vacuum and purified by column chromatograph (eluant: ethyl acetate/MeOH=50:1) to afford product 45 mg as white solid, 90% yield.

Example 19

Preparation of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate

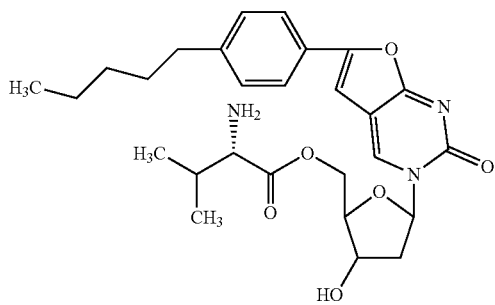 [SMILES: CCCCCc1ccc(-c2cc3cn(C4CC(O)C(COC(=O)[C@@H](N)C(C)C)O4)c(=O)nc3o2)cc1]

To a 500 mL flask was added DCM 200 mL, (S)-((2R,3S,5R)-3-hydroxy) 5-(2-oxo-6-(4-pentylphenyl)furo[2,3-d]pyrimidin-3 (2H)-yl)-tetrahydrofuran-2-yl)methyl 2-(((9H-fluoren-9-yl)methoxy)carbonylamino)-3-methylbutanoate 19.7 g (27.4 mmol), The reaction mixture was cooled, and 8.3 g DBU (54.8 mmol) was added to the reaction mixture. The reaction was stirred at rt for 2 h until TLC showed the end of the reaction.

TLC: eluant: DCM/methanol=6:1;

(S)-((2R,3S,5R)-3-hydroxy-5-(2-oxo-6-(4-pentylphenyl)furo[2,3-d]pyrimidin-3(2H)-yl)-tetrahydrofuran-2-yl)methyl 2-(((9H-fluoren-9-yl)methoxy)carbonylamino)-3-methyl butanoate:

$R_f$=0.55;

(S)-((2R,3S,5R)-(3-hydroxy-5-(2-oxo-6-(4-pentylphenyl)furo[2,3-d]pyrimidin-3(2H)-yl)-tetrahydrofuran-2-yl))methyl 2-amino-3-methylbutanoate:

$R_f$=0.24.

The above reaction mixture was cooled below 5° C. and was added with 20% of HCl IPA solution until pH 1~4. The mixture was stirred for additional 1 h and was filtered. The filter cake was washed with dichloromethane. Desired crude product was obtained. The yield was 90% and the purity was 97%. The crude product was recrystallized with methanol/dichloromethane/MTBE to give the desired pure product.

Example 20

Recrystallization of (S)-((2R,3S,5R)-(3-Hydroxy-5-(2-oxo-6-(4-pentylphenyl)furo[2,3-d]pyrimidin-3 (2H)-yl)-tetrahydrofuran-2-yl)methyl 2-amino-3-methylbutanoate Hydrochloride

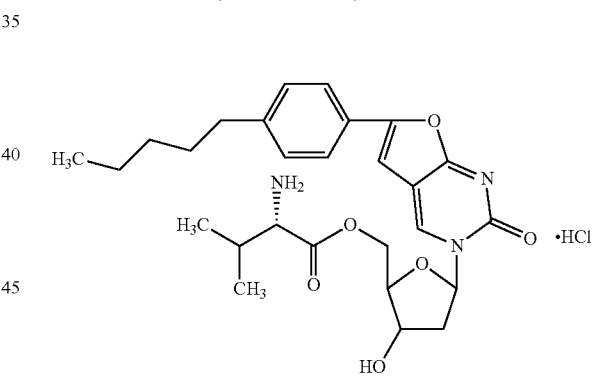

To a 500 mL three-necked flask was added 1 g (S)-((2R,3S,5R)-(3-hydroxy-5-(2-oxo-6-(4-pentylphenyl)furo[2,3-d]pyrimidin-3 (2H)-yl)-tetrahydrofuran-2-yl)methyl 2-amino-3-methylbutanoate hydrochloride, 30 mL methanol, and 15 mL dichloromethane. The mixture was heated at reflux until the solution became clear. The solution was filtered and the filtrate was evaporated to ⅓~¼ vol, 15 mL DCM was added to the residue and the mixture was then evaporated to ½~⅓ vol. 15 mL MTBE was added to the residue at 40~45° C. to give 0.85 g pure product.

Example 21

Recrystallization of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

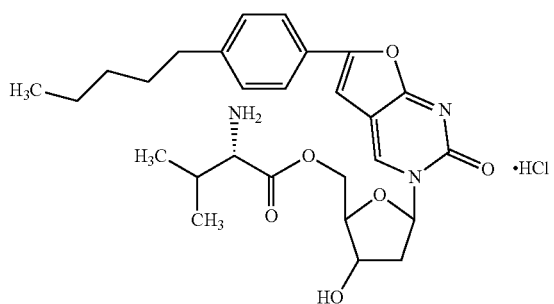 [SMILES: CCCCCc1ccc(-c2cc3cn(C4CC(O)C(COC(=O)[C@@H](N)C(C)C)O4)c(=O)nc3o2)cc1 ; Cl]

To a 100 mL three-necked flask was added 1.0 g of (S)-((2R,3S,5R)-(3-hydroxy-5-(2-oxo-6-(4-pentylphenyl)furo[2,3-d]pyrimidin-3 (2H)-yl)-tetrahydro-furan-2-yl)methyl-2-amino-3-methylbutanoate hydrochloride, 30 mL of methanol, 15 mL of dichloromethane, the mixture was heated at reflux until the solution became clear. The solution was filtered and the filtrate was stirred for overnight and then evaporated to ⅓~¼ of the original volume, and MTBE was added to the residue at 30~45° C. The mixture was cooled to 0~10° C. and filtered to give 0.91 g pure product.

Example 22

Recrystallization of (S)-((2R,3S,5R)-(3-Hydroxy-5-(2-oxo-6-(4-pentylphenyl)furo[2,3-d]pyrimidin-3 (2H)-yl)-tetrahydrofuran-2-yl)methyl 2-amino-3-methylbutanoate Hydrochloride

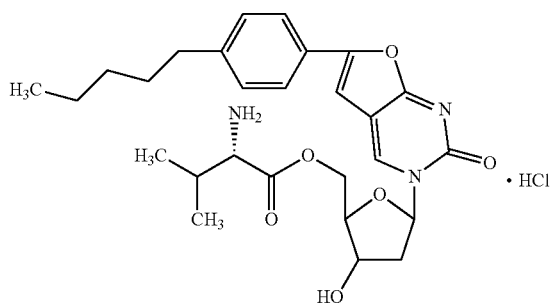 [SMILES: CCCCCc1ccc(-c2cc3cn(C4CC(O)C(COC(=O)[C@@H](N)C(C)C)O4)c(=O)nc3o2)cc1 ; Cl]

Method A.

To a 50 L three-necked flask was added 1.2 kg of (S)-((2R,3S,5R)-(3-hydroxy-5-(2-oxo-6-(4-pentylphenyl)furo[2,3-d]pyrimidin-3(2H)-yl)-tetrahydrofuran-2-yl)methyl 2-amino-3-methylbutanoate hydrochloride, 36 L methanol, 18 L dichloromethane, the mixture was heated at reflux until the solution became clear. The solution was filtered and the filtrated was evaporated to ⅓~¼ of the original volume, and MTBE was added to the residue at 30~45° C. to give 1.1 kg pure product.

Method B.

To a 500 mL three-necked flask was added 5.0 g of (S)-((2R,3S,5R)-(3-hydroxy-5-(2-oxo-6-(4-pentylphenyl)furo[2,3-d]pyrimidin-3 (2H)-yl)-tetrahydro-furan-2-yl)methyl-2-amino-3-methylbutanoate hydrochloride, 70 mL of THF and 30 mL of H₂O, the mixture was heated at 35~45° C. until the solution became clear. The solution was filtered and the filtrate was evaporated to ½~⅓ of the original volume at 30~45° C. The mixture was cooled to 0~10° C. and filtered to give 4.2 g pure product.

Method C.

To a 500 mL three-necked flask was added 5.0 g of (S)-((2R,3S,5R)-(3-hydroxy-5-(2-oxo-6-(4-pentylphenyl)furo[2,3-d]pyrimidin-3 (2H)-yl)-tetrahydro-furan-2-yl)methyl-2-amino-3-methylbutanoate hydrochloride and 75 mL of DMF, the mixture was heated at 65~75° C. until the solution became clear. The solution was filtered and the filtrate was cooled to 20~30° C. 75 mL DCM was added to the mixture, and then stirred at 0~10° C. for 4 h. The mixture was filtered to give 4.0 g pure product.

Method D.

To a 10 L reactor was added 1200 g of DMSO, and this was heated to 50~55° C. To this was added 158 g crude (S)-((2R,3S,5R)-(3-hydroxy-5-(2-oxo-6-(4-pentylphenyl)furo[2,3-d]pyrimidin-3(2H)-yl)-tetrahydrofuran-2-yl)methyl 2-amino-3-methylbutanoate hydrochloride. The mixture was stirred until the solution became clear. The solution was filtered. The cake was washed with 90 g of DMSO. The filtrate was cooled to 30~35° C., and 4000 g of DCM was added to the mixture. The mixture was stirred at 20~30° C. for 30 min, then cooled to 0~10° C. with stirring for 4 h. The mixture was centrifuged. The wet cake was washed twice with DCM (420 g×2). The solid residue was slurried with 2130 g of EA at 20~30° C. for 2 h. The mixture was centrifuged. The cake was washed with 425 g of EA. The solid was dried at 30~35° C. under reduced pressure for 24 h. After drying, a white powder (117 g, 73.8% yield) was obtained which assayed at 99.7% purity.

Example 23

Preparation of Form II of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

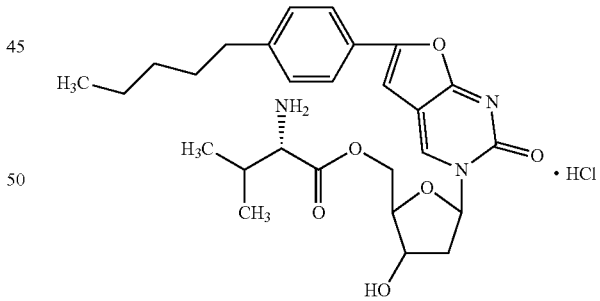

In a 1 L reactor, 0.126 g of NaHCO₃ (0.02 equiv) was dissolved in 400 mL of H₂O (10 vol). A mixture of 40 g of polymorph I and polymorph II of (S)-((2R,3S,5R)-(3-hydroxy-5-(2-oxo-6-(4-pentylphenyl)furo[2,3-d]pyrimidin-3 (2H)-yl)-tetrahydrofuran-2-yl)methyl 2-amino-3-methylbutanoate hydrochloride was charged into the reactor at 25-35° C. and stirred for 3-4 h. The mixture was filtered. The cake was washed with H₂O (40 mL×2). The wet cake was re-slurried with 400 mL of IPA below 10° C. for 1-2 h. The mixture was centrifuged. The cake was washed with IPA (40 mL×3). The solid was dried under vacuum at 45° C.-55° C. for 24 h. 37.5 g of white powder in 93.8% yield and 99.48% purity were achieved.

Example 24

Polymorph Form II Preparation of (R)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

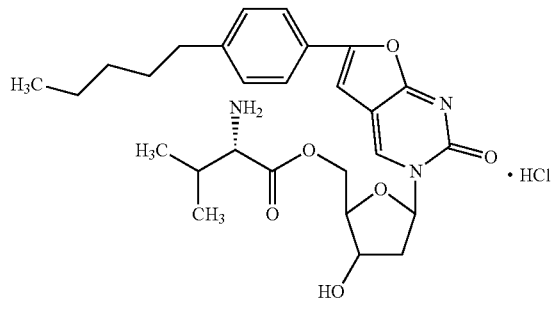 [SMILES: CCCCCc1ccc(-c2cc3cn(C4CC(O)C(COC(=O)[C@@H](N)C(C)C)O4)c(=O)nc3o2)cc1 ; Cl]

In a 500 mL reactor, 0.031 g of NaHCO$_3$ (0.01 equiv) was dissolved in 200 mL of H$_2$O (10 vol). A mixture of 20 g of polymorph I and polymorph II of (S)-((2R,3S,5R)-(3-hydroxy-5-(2-oxo-6-(4-pentylphenyl)furo[2,3-d]pyrimidin-3 (2H)-yl)-tetrahydrofuran-2-yl)methyl 2-amino-3-methylbutanoate hydrochloride was charged into the reactor at 25-35° C. and stirred for 3-4 h. The mixture was filtered. The cake was washed with H$_2$O (20 mL×2). The wet cake was re-slurried with 200 mL of IPA, and maintained below 10° C. for 1-2 h. The mixture was centrifuged. The cake was washed with IPA (20 mL×3). The solid was dried under vacuum at 45° C.-55° C. for 24 h. A white powder (19.0 g, 95.0% yield) was obtained in 99.30% purity.

Example 25

Preparation of Form II of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

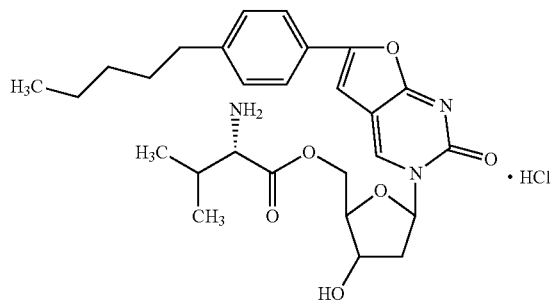 [SMILES: CCCCCc1ccc(-c2cc3cn(C4CC(O)C(COC(=O)[C@@H](N)C(C)C)O4)c(=O)nc3o2)cc1 ; Cl]

In a 100 mL reactor, 0.023 g of NaHCO$_3$ (0.05 equiv) was dissolved in 30 mL of H$_2$O (10 vol). A mixture of 3 g of polymorph I and polymorph II of (S)-((2R,3S,5R)-(3-hydroxy-5-(2-oxo-6-(4-pentylphenyl)furo[2,3-d]pyrimidin-3 (2H)-yl)-tetrahydrofuran-2-yl)methyl 2-amino-3-methylbutanoate hydrochloride was charged into the reactor at 25-35° C. and stirred for 3-4 h. The mixture was filtered. The cake was washed with H$_2$O (3 mL×2). The wet cake was re-slurried with 30 mL of IPA at 0-10° C. for 1-2 h. The mixture was centrifuged. The cake was washed with IPA (3 mL×3). The solid was dried under vacuum at 45° C.-55° C. for 24 h. A white powder (2.4 g) was obtained in 80.0% yield and 99.40% purity.

Example 26

Preparation of Form II of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

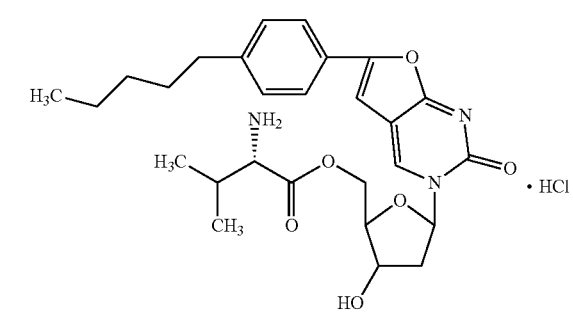 [SMILES: CCCCCc1ccc(-c2cc3cn(C4CC(O)C(COC(=O)[C@@H](N)C(C)C)O4)c(=O)nc3o2)cc1 ; Cl]

In a 100 mL reactor, 0.047 g of NaHCO$_3$ (0.1 equiv) was dissolved in 30 mL of H$_2$O (10 vol). A mixture of 3 g of polymorph I and polymorph II of (S)-((2R,3S,5R)-(3-hydroxy-5-(2-oxo-6-(4-pentylphenyl)furo[2,3-d]pyrimidin-3 (2H)-yl)-tetrahydrofuran-2-yl)methyl 2-amino-3-methylbutanoate hydrochloride was charged into the reactor at 25-35° C. and stirred for 3-4 h. The mixture was filtered. The cake was washed with H$_2$O (3 mL×2). The wet cake was re-slurried with 30 mL of IPA at 0-10° C. for 1-2 h. The mixture was centrifuged. The cake was washed with IPA (3 mL×3). The solid was dried under vacuum at 45° C.-55° C. for 24 h. A white powder (2.4 g) was obtained in 80.0% yield and 99.40% purity.

Example 27

Preparation of Form II of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

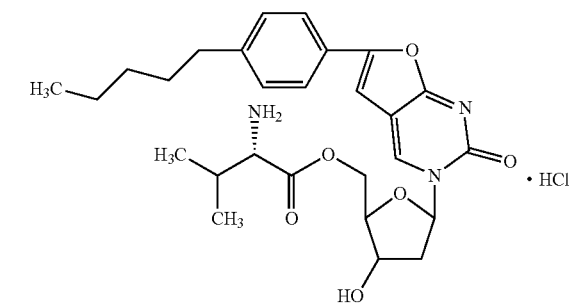 [SMILES: CCCCCc1ccc(-c2cc3cn(C4CC(O)C(COC(=O)[C@@H](N)C(C)C)O4)c(=O)nc3o2)cc1 ; Cl]

In a 100 mL reactor, 3 g of polymorph I and polymorph II mixture of (S)-((2R,3S,5R)-(3-hydroxy-5-(2-oxo-6-(4-pentylphenyl)furo[2,3-d]pyrimidin-3 (2H)-yl)-tetrahydrofuran-2-yl)methyl 2-amino-3-methylbutanoate hydrochloride was charged into 30 mL of $H_2O$ (10 vol) at 25-35° C. and stirred for 3-4 h. The mixture was filtered and the cake was washed with $H_2O$ (3 mL×2). The wet cake was re-slurried with 30 mL of IPA at 0-10° C. for 1-2 h. The mixture was centrifuged. The cake was washed with IPA (3 mL×3). The solid was dried under vacuum at 45° C.-55° C. for 24 h. A white powder (2.5 g) was obtained in 83.3% yield and 99.42% purity.

Example 28

Preparation of Form II of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

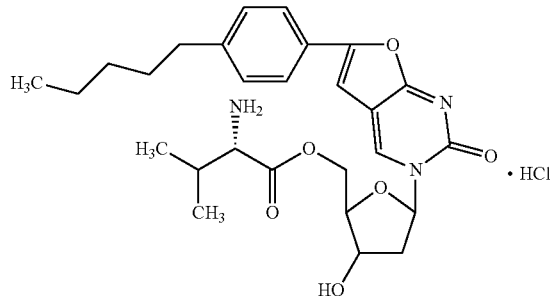 [SMILES: CCCCCc1ccc(-c2cc3cn(C4CC(O)C(COC(=O)[C@@H](N)C(C)C)O4)c(=O)nc3o2)cc1 ; Cl]

In a 100 mL reactor, 3 g of polymorph I and polymorph II mixture of (S)-((2R,3S,5R)-(3-hydroxy-5-(2-oxo-6-(4-pentylphenyl)furo[2,3-d]pyrimidin-3 (2H)-yl)-tetrahydrofuran-2-yl)methyl 2-amino-3-methylbutanoate hydrochloride was charged into 30 mL of $H_2O$ (10 vol) at 25-35° C. and stirred for 3-4 h. The mixture was filtered and the cake was washed with $H_2O$ (3 mL×2). The solid was dried under vacuum at 45° C.-55° C. for 24 h. A white powder (2.8 g) was obtained in 93% yield and 99.2% purity.

Example 29

Preparation of Form II of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

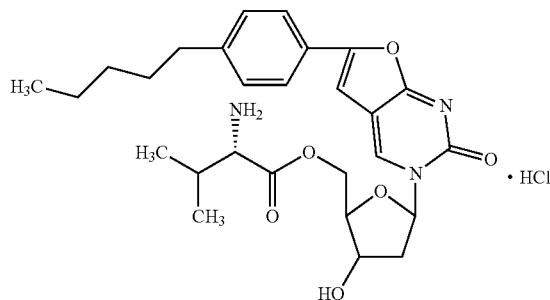 [SMILES: CCCCCc1ccc(-c2cc3cn(C4CC(O)C(COC(=O)[C@@H](N)C(C)C)O4)c(=O)nc3o2)cc1 ; Cl]

In a 100 mL reactor, 3 g of polymorph I and polymorph II mixture of (S)-((2R,3S,5R)-(3-hydroxy-5-(2-oxo-6-(4-pentylphenyl)furo[2,3-d]pyrimidin-3 (2H)-yl)-tetrahydrofuran-2-yl)methyl 2-amino-3-methylbutanoate hydrochloride was charged into 27 mL of $H_2O$ (9 vol) and 3 mL of acetonitrile (1 vol) between 25-35° C. and stirred for 3-4 h. The mixture was filtered and the cake was washed with $H_2O$ (3 mL×2). The solid was dried under vacuum at 45° C.-55° C. for 24 h. A white powder (2.85 g) was obtained in 95% yield and 99.2% purity.

Example 30

Preparation of Form II of (S)-((2R,3S,5R)-(3-Hydroxy-5-(2-oxo-6-(4-pentylphenyl)furo[2,3-d]pyrimidin-3(2H)-yl)-tetrahydrofuran-2-yl)methyl 2-amino-3-methylbutanoate Hydrochloride

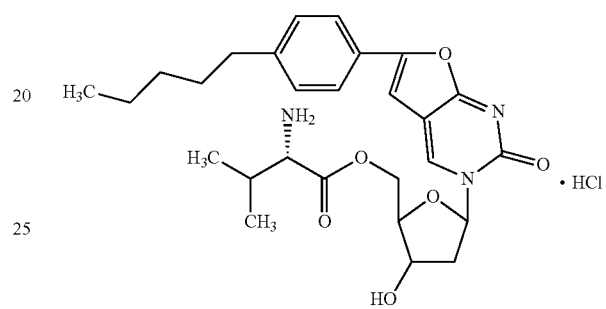

In a 100 mL reactor, 3.0 g of polymorph I and polymorph II mixture of (S)-((2R,3S,5R)-(3-hydroxy-5-(2-oxo-6-(4-pentylphenyl)furo[2,3-d]pyrimidin-3 (2H)-yl)-tetrahydrofuran-2-yl)methyl 2-amino-3-methylbutanoate hydrochloride was charged into 12 mL of $H_2O$ (4 vol) at room temperature. The mixture was allowed to stand for 3 days without agitation. The mixture was filtered and the cake was washed with $H_2O$ (3 mL×2). The solid was dried under vacuum at 45° C.-55° C. for 24 h. A white powder (2.9 g) was obtained in 96.7% yield and 99.4% purity.

Example 31

Figure 2:
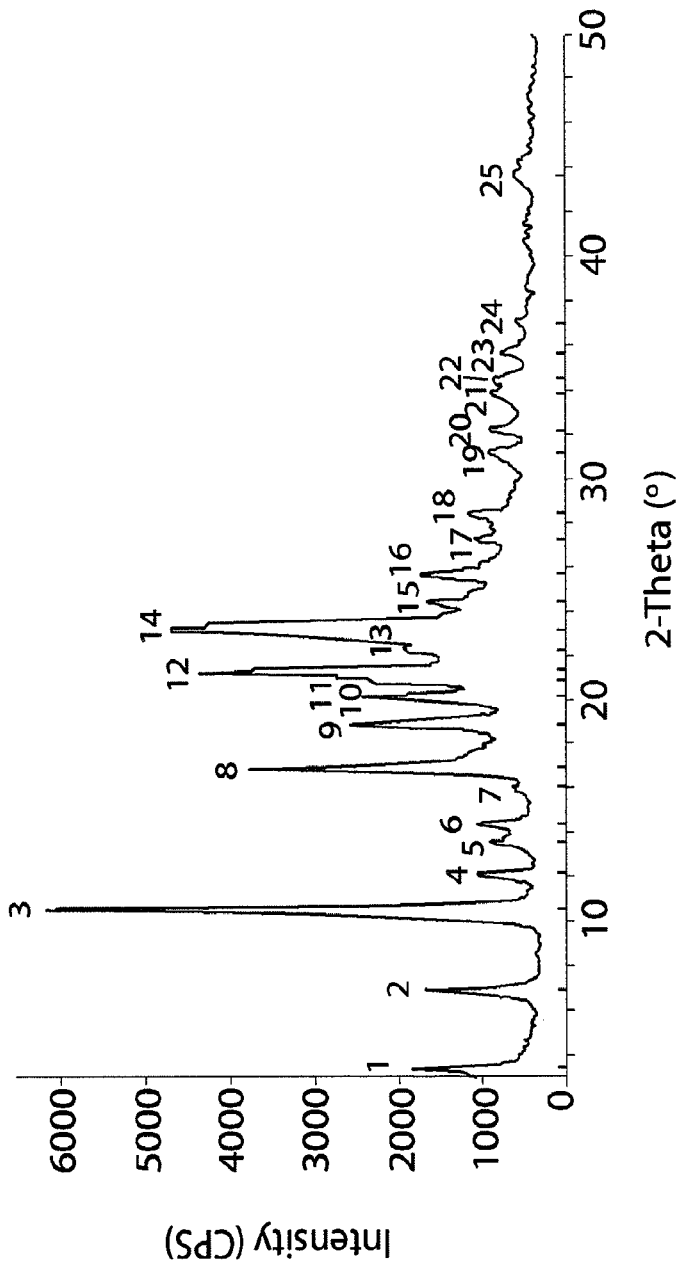
FIG. 2 is the X-Ray Powder Diffraction (XRPD) pattern for Polymorphic Form (II) of the hydrochloride salt of Compound 4.

To distinguish the Mixture of the two Polymorphic Forms [(I) and (II)] and the Polymorphic Form II, X-Ray Powder Diffraction (XRPD) patterns were obtained. These would show the main characteristic peaks as Peak-1 (2–Theta=10.2) and Peak-2 (2–Theta=22.2). Both of them exist in the Mixture of the two Polymorphic Forms [(I) and (II)] (as shown in FIG. 1), but they have disappeared and are thus not present in the Polymorphic Form II (as shown in FIG. 2). A comparison showing the peaks is provided in FIG. 3. Peak data is included in the Table below.

| Characteristic Peaks | 2-Theta | |
| --- | --- | --- |
| | Polymorph I and Polymorph II Mixture (Picture-1) | Polymorph II (Picture-2 |
| Peak-1 | 3.6 | 3.42 |
| | 7.28 | 6.879 |
| | 10.22 | N/D |
| | 10.62 | 0.599 |
| | 2.239 | 12.121 |
| | 13.638 | 13.56 |
| | 14.56 | 14.399 |
| | 16.86 | 16.9 |
| | 17.702 | 17.559 |

| | 2-Theta | |
|---|---|---|
| Characteristic Peaks | Polymorph I and Polymorph II Mixture (Picture-1) | Polymorph II (Picture-2 |
| | 18.301 | 18.859 |
| | 20.18 | 20.14 |
| | 21.321 | 21.32 |
| Peak-2 | 22.2 | N/D |
| | 23.04 | 23.14 |

What is claimed is:

1. A process for the synthesis of a compound of Formula (IV) from a compound of Formula (IIIa):

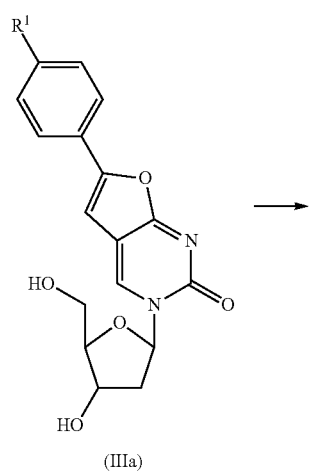

(IIIa)

→

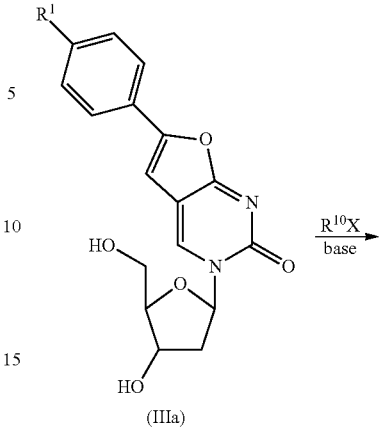

(IIIa)

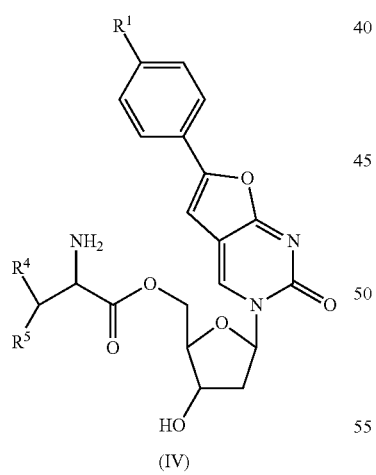

(IV)

wherein:

$R^1$ is $C_1$-$C_6$ alkyl; and $R^4$ and $R^5$ are each independently H or $C_1$-$C_2$ alkyl, or a pharmaceutically acceptable salt thereof, comprising the steps of (1) protecting the primary hydroxyl group in a compound of Formula (IIIa) to form a compound of Formula (V),

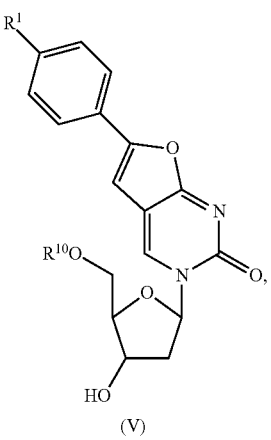

(V)

comprising reacting the primary hydroxyl group in a compound of Formula (IIIa) with $R^{10}X$ in the optional presence of a base, wherein:

$R^{10}$ is trityl, 4,4'-dimethoxytrityl, tert-butyldimethylsilyl, diphenylmethylsilyl, or tert-butyldiphenylsilyl; and X is a leaving group;

(2) protecting the secondary hydroxyl group in a compound of Formula (V) to form a compound of Formula (VI),

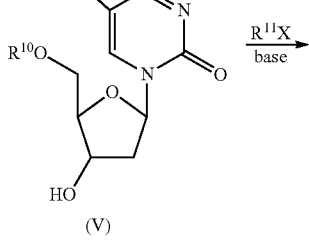

(V)

-continued

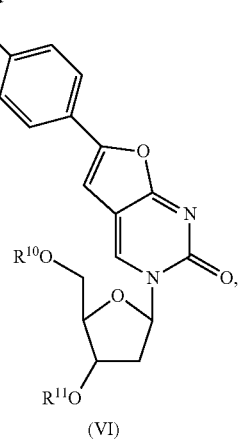
(VI)

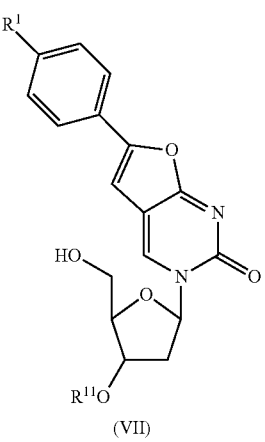
(VII)
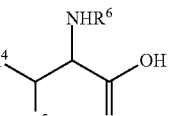
(X)
coupling agent → comprising reacting a compound of Formula (V) with $R^{11}X$ in the optional presence of a base, wherein:
- $R^{11}$ is $C_1$-$C_6$ alkanoyl, halogen substituted alkanoyl, optionally substituted aroyl, optionally substituted benzyl, carboxylbenzyl, or diphenylmethyl; and
- X is a leaving group;

(3) deprotecting the primary hydroxyl group in a compound of Formula (VI) to form a compound of Formula (VII),

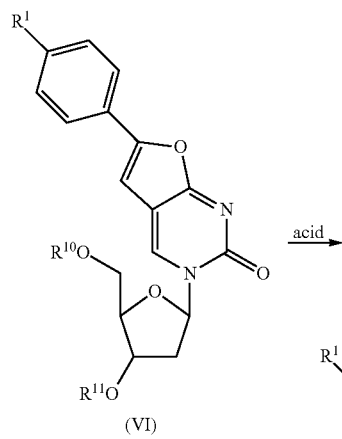
(VI)
acid →

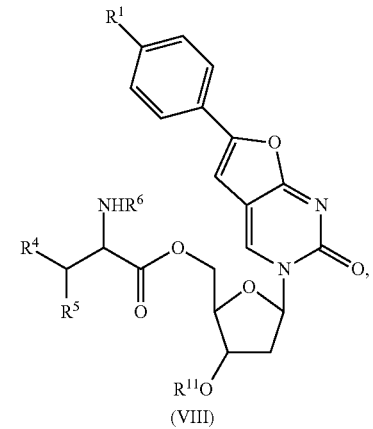
(VIII)

comprising esterifying the primary hydroxyl group in a compound of Formula (VII) with a compound of Formula (X), optionally in the presence of a coupling or dehydrating agent and/or a base, to form a compound of Formula (VIII), wherein:
- $R^6$ is tert-butyloxycarbonyl, 9-fluorenylmethyloxycarbonyl, or carboxybenzyl;

(5) deprotecting the secondary hydroxyl group and amino acid group in a compound of Formula (VIII) to form a compound of Formula (IV),

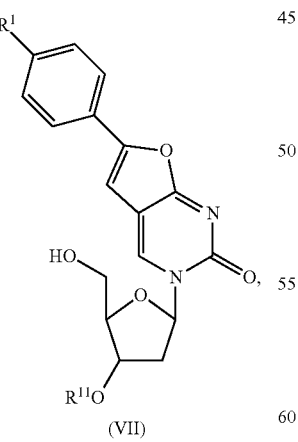
(VII)

comprising reacting a compound of Formula (VI) with an acid;

(4) esterifying the primary hydroxyl group in a compound of Formula (VII) with a compound of Formula (X) to form a compound of Formula (VIII),

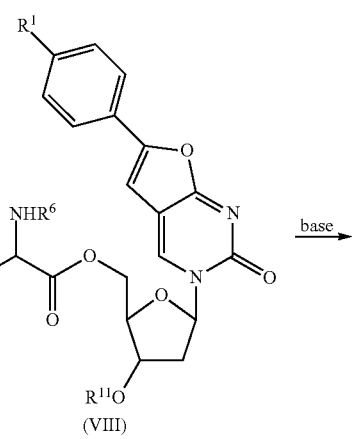
(VIII)
base →

-continued

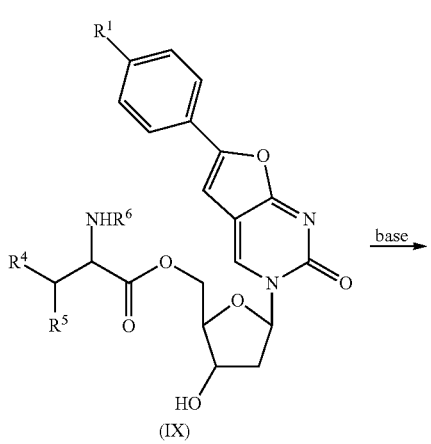
(IX)

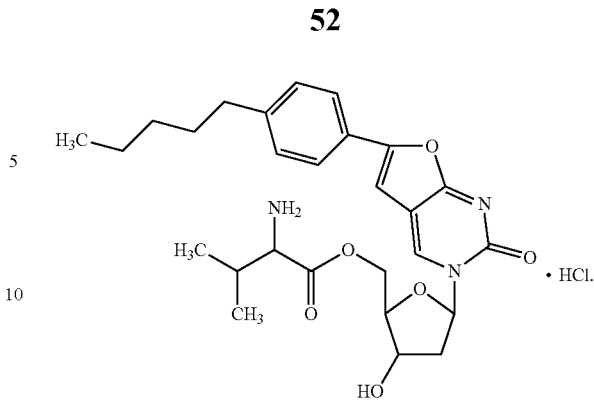

8. The process of claim 1, wherein the compounds in steps (1)-(4) are selected from a compound of Formula (V), which is selected from

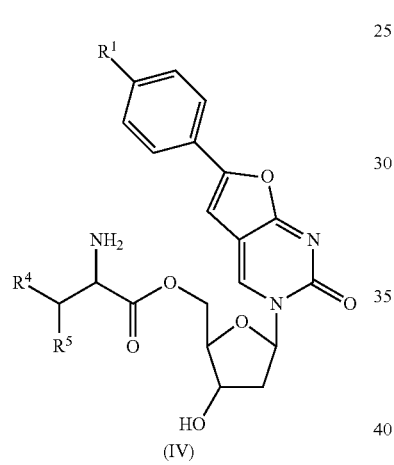
(IV)

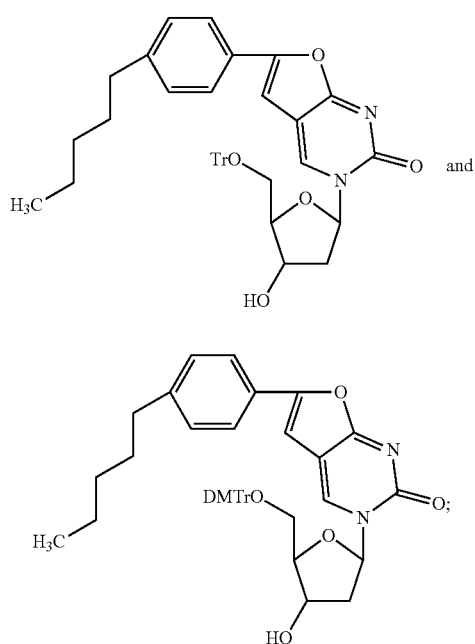

comprising deprotecting $R^{11}$ and $R^6$ in a compound of Formula (VIII), to provide a compound of Formula (IV); and (6) optionally converting a compound of Formula (IV) to a pharmaceutically acceptable salt thereof.

2. The process of claim 1, wherein in step (1) X is halo, optionally substituted arylsulfonyl, or $C_1$-$C_6$ alkylsulfonyl.

3. The process of claim 2, wherein X is halo or tosyl.

4. The process of claim 3, wherein X is selected from the group consisting of Cl, Br, and I.

5. The process of claim 1, wherein in step (3) the acid is selected from the group consisting of acetic acid, hydrochloric acid, trichloroacetic acid, and trifluoroacetic acid.

6. The process of claim 1, wherein:
$R^1$ is n-pentyl; and
$R^4$ and $R^5$ are each methyl.

7. The process of claim 1, wherein the pharmaceutically acceptable salt of a compound of Formula (IV) is a compound of Formula (VI), which is selected from

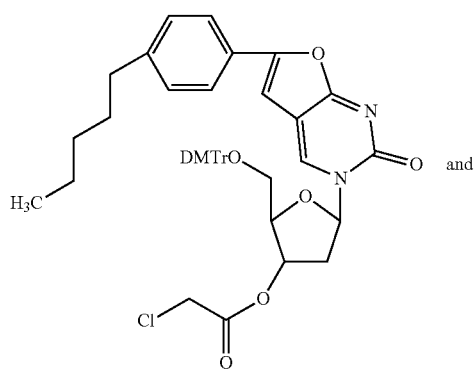

-continued

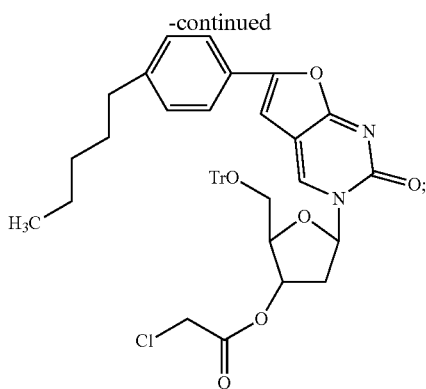

a compound of Formula (VII), which is

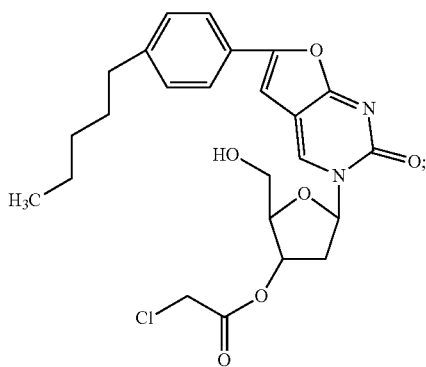 [SMILES: CCCCCc1ccc(-c2cc3cn(C4CC(OC(=O)CCl)C(CO)O4)c(=O)nc3o2)cc1]

and
a compound of Formula (VIII), which is

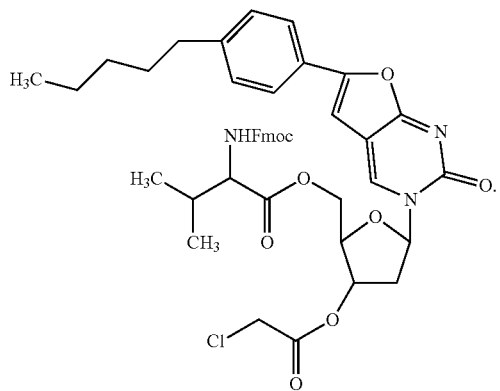

9. A process for the purification of (S)-((2R,3S,5R)-(3-hydroxy-5-(2-oxo-6-(4-pentylphenyl)furo[2,3-d]pyrimidin-3(2H)-yl)-tetrahydrofuran-2-yl)methyl 2-amino-3-methylbutanoate hydrochloride, comprising the steps of
1) dissolving crude (S)-((2R,3S,5R)-(3-hydroxy-5-(2-oxo-6-(4-pentylphenyl)furo[2,3-d]pyrimidin-3(2H)-yl)-tetrahydrofuran-2-yl)methyl 2-amino-3-methylbutanoate hydrochloride in a suitable solvent to form a solution;
2) adding sufficient anti-solvent to the solution to effect formation of a solid precipitate; and
3) isolating the solid precipitated (S)-((2R,3S,5R)-(3-hydroxy-5-(2-oxo-6-(4-pentylphenyl)furo[2,3-d]pyrimidin-3(2H)-yl)-tetrahydrofuran-2-yl)methyl 2-amino-3-methylbutanoate hydrochloride.

10. The process of claim 9, wherein the suitable solvent is selected from DMSO, DMF, NMP, methanol/DCM, DMF/DCM, DMSO/DCM, methanol/DCM/MTBE, and THF/$H_2O$.

11. A form (II) polymorph of (S)-((2R,3S,5R)-(3-hydroxy-5-(2-oxo-6-(4-pentylphenyl)furo[2,3-d]pyrimidin-3(2H)-yl)-tetrahydrofuran-2-yl)methyl 2-amino-3-methylbutanoate hydrochloride, characterized by an X-ray powder diffraction pattern including characteristic peaks at about 3.4, 6.9, 0.6, 12.1, 13.6, 14.4, 16.9, 17.6, 18.9, 20.1, 21.3, and 23.1 degrees 2θ.

12. The form (II) polymorph of claim 11, which generates the X-ray powder diffraction pattern depicted in FIG. 2.

13. A process for the transformation of a form (I) polymorph or a mixture of a form (I) polymorph and a form (II) polymorph of (S)-((2R,3S,5R)-(3-hydroxy-5-(2-oxo-6-(4-pentylphenyl)furo[2,3-d]pyrimidin-3(2H)-yl)-tetrahydrofuran-2-yl)methyl 2-amino-3-methylbutanoate hydrochloride into the form (II) polymorph, wherein:
the form (I) polymorph is characterized by an X-ray powder diffraction pattern including characteristic peaks at about 3.6, 7.3, 10.2, 10.6, 2.2, 13.6, 14.6, 16.9, 17.7, 18.3, 20.1, 21.3, 22.2, and 23.0 degrees 2θ; and
the form (II) polymorph is characterized by an X-ray powder diffraction pattern including characteristic peaks at about 3.4, 6.9, 0.6, 12.1, 13.6, 14.4, 16.9, 17.6, 18.9, 20.1, 21.3, and 23.1 degrees 2θ,
comprising the steps of
(1) allowing the form (I) polymorph or the mixture of the form (I) polymorph and the form (II) polymorph to age in a suitable solvent or solvent mixture; and
(2) isolating the resulting form (II) polymorph.

14. The process of claim 13, further comprising the addition of a base in step (1).

15. The process of claim 14, wherein the base is selected from sodium bicarbonate, sodium carbonate, triethylamine, diisopropylethylamine, and piperidine.

* * * * *